(12) United States Patent
Davis et al.

(10) Patent No.: US 11,844,650 B1
(45) Date of Patent: *Dec. 19, 2023

(54) THERMOACOUSTIC MEASUREMENT PROBE

(71) Applicants: ENDRA Life Sciences Inc., Ann Arbor, MI (US); Duke University, Durham, NC (US)

(72) Inventors: Christopher Nelson Davis, Ann Arbor, MI (US); Paolo Maccarini, Durham, NC (US); Idan Steinberg, Superior Charter Township, MI (US); Michael M. Thornton, London (CA)

(73) Assignees: ENDRA Life Sciences Inc., Ann Arbor, MI (US); Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/130,192

(22) Filed: Apr. 3, 2023

Related U.S. Application Data

(63) Continuation-in-part of application No. 17/946,700, filed on Sep. 16, 2022, now Pat. No. 11,619,613.

(51) Int. Cl.
| | |
|---|---|
| *G01N 29/24* | (2006.01) |
| *A61B 8/08* | (2006.01) |
| *G01N 29/04* | (2006.01) |
| *G01N 29/06* | (2006.01) |
| *G02F 1/225* | (2006.01) |

(52) U.S. Cl.
CPC .......... *A61B 8/485* (2013.01); *G01N 29/043* (2013.01); *G01N 29/0654* (2013.01); *G01N 29/2431* (2013.01); *G02F 1/2255* (2013.01)

(58) Field of Classification Search
CPC .. A61B 8/485; G01N 29/043; G01N 29/0654; G01N 29/2431; G01N 29/2418; G01N 29/2437; G01N 29/24; G01N 29/2462; G01N 29/2443; H01P 11/002; G02F 1/2255

See application file for complete search history.

(56) References Cited

U.S. PATENT DOCUMENTS

| | | | |
|---|---|---|---|
| 11,304,606 B2 * | 4/2022 | Davis | A61B 5/201 |
| 11,369,272 B1 * | 6/2022 | Davis | H01P 3/123 |
| 11,619,613 B1 * | 4/2023 | Davis | G01N 29/2431 |
| | | | 73/643 |
| 2013/0296683 A1 * | 11/2013 | Herzog | A61B 5/0095 |
| | | | 600/407 |

* cited by examiner

*Primary Examiner* — Suman K Nath
(74) *Attorney, Agent, or Firm* — Stanley E. Jelic

(57) ABSTRACT

A thermoacoustic measurement probe includes an open-ended hollow radio-frequency (RF) waveguide; at least two RF feeds positioned within the open-ended hollow RF waveguide, wherein each RF feed is configured to provide RF energy; and a thermoacoustic transducer, wherein the open-ended hollow RF waveguide, in the form of a sleeve, surrounds and is mechanically joined to the thermoacoustic transducer.

20 Claims, 40 Drawing Sheets

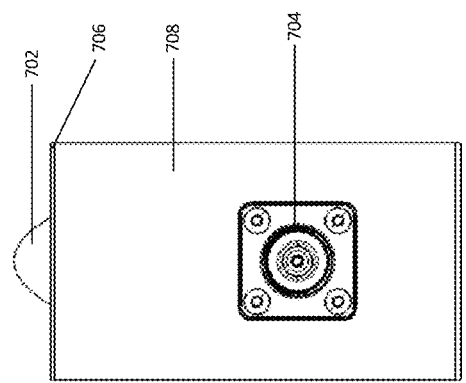
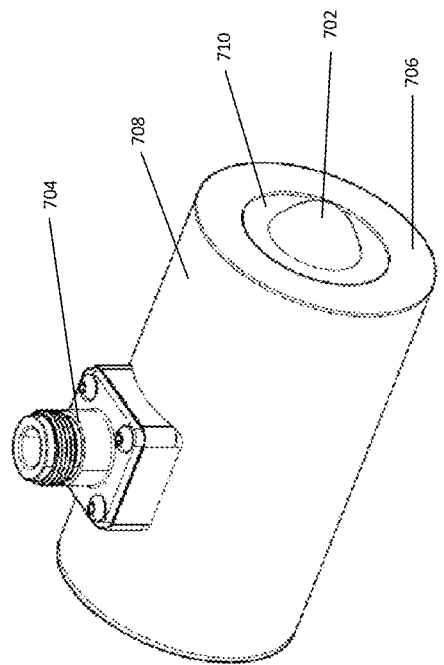
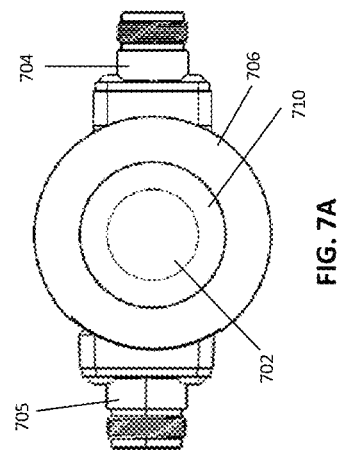
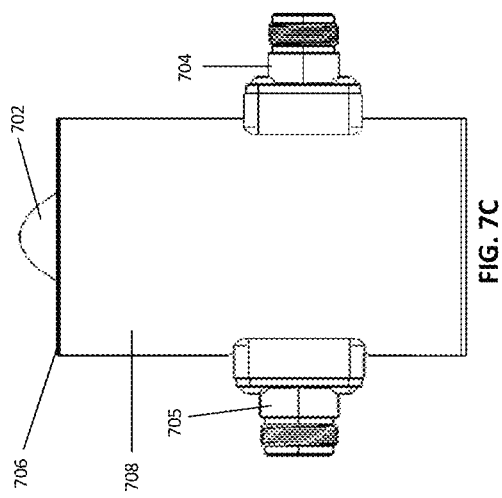
FIG. 7B
FIG. 7D
FIG. 7A
FIG. 7C

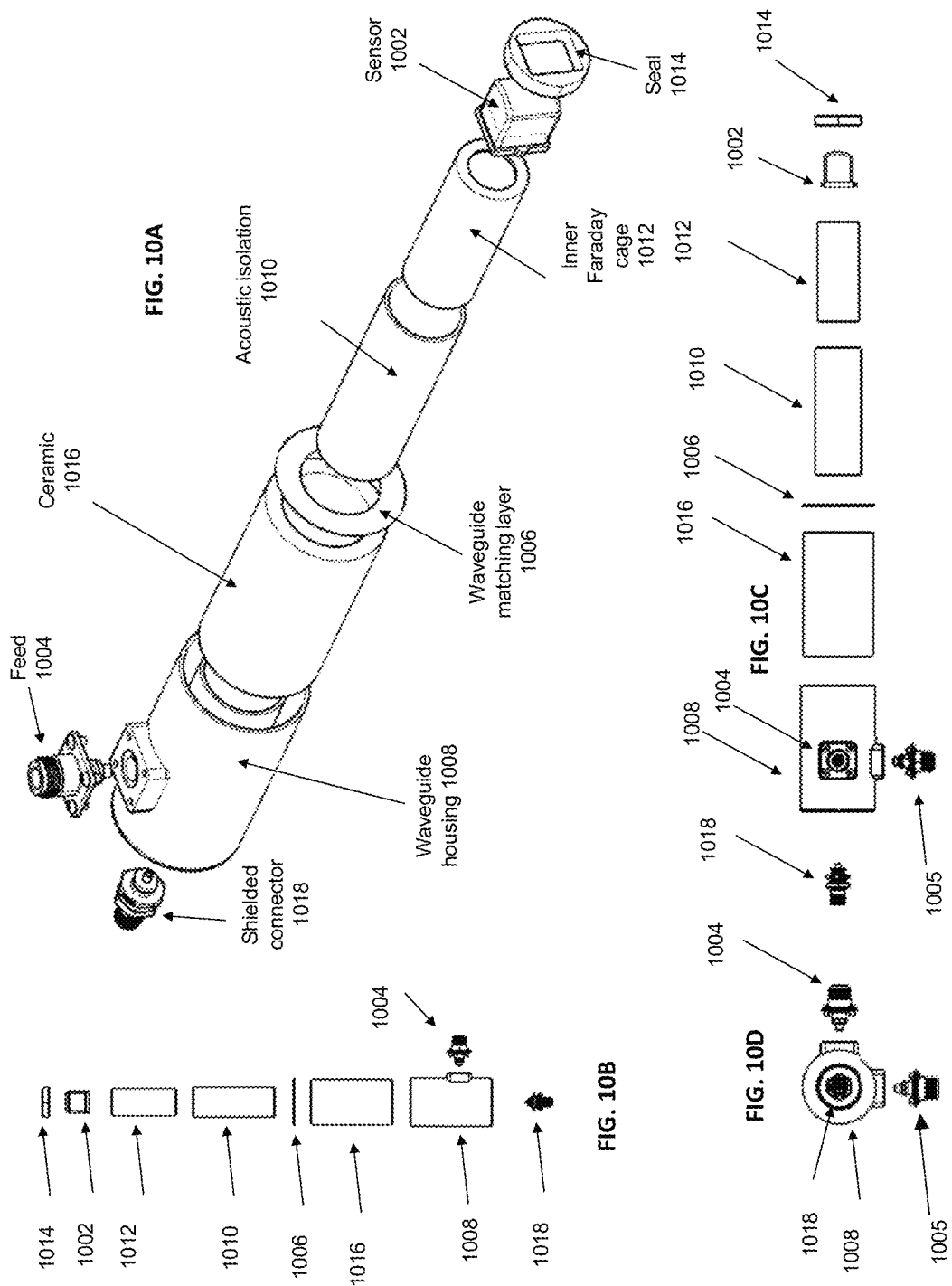

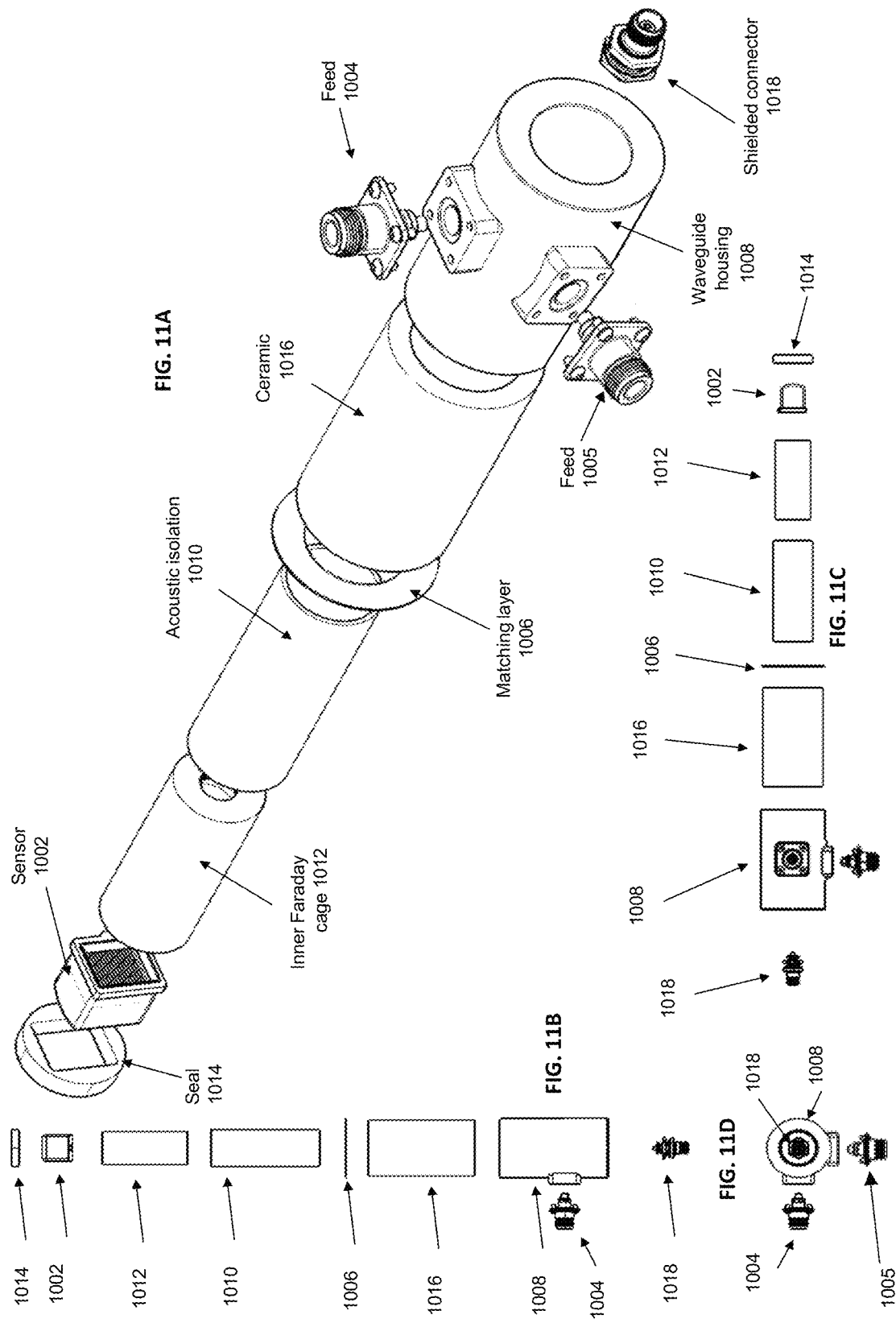

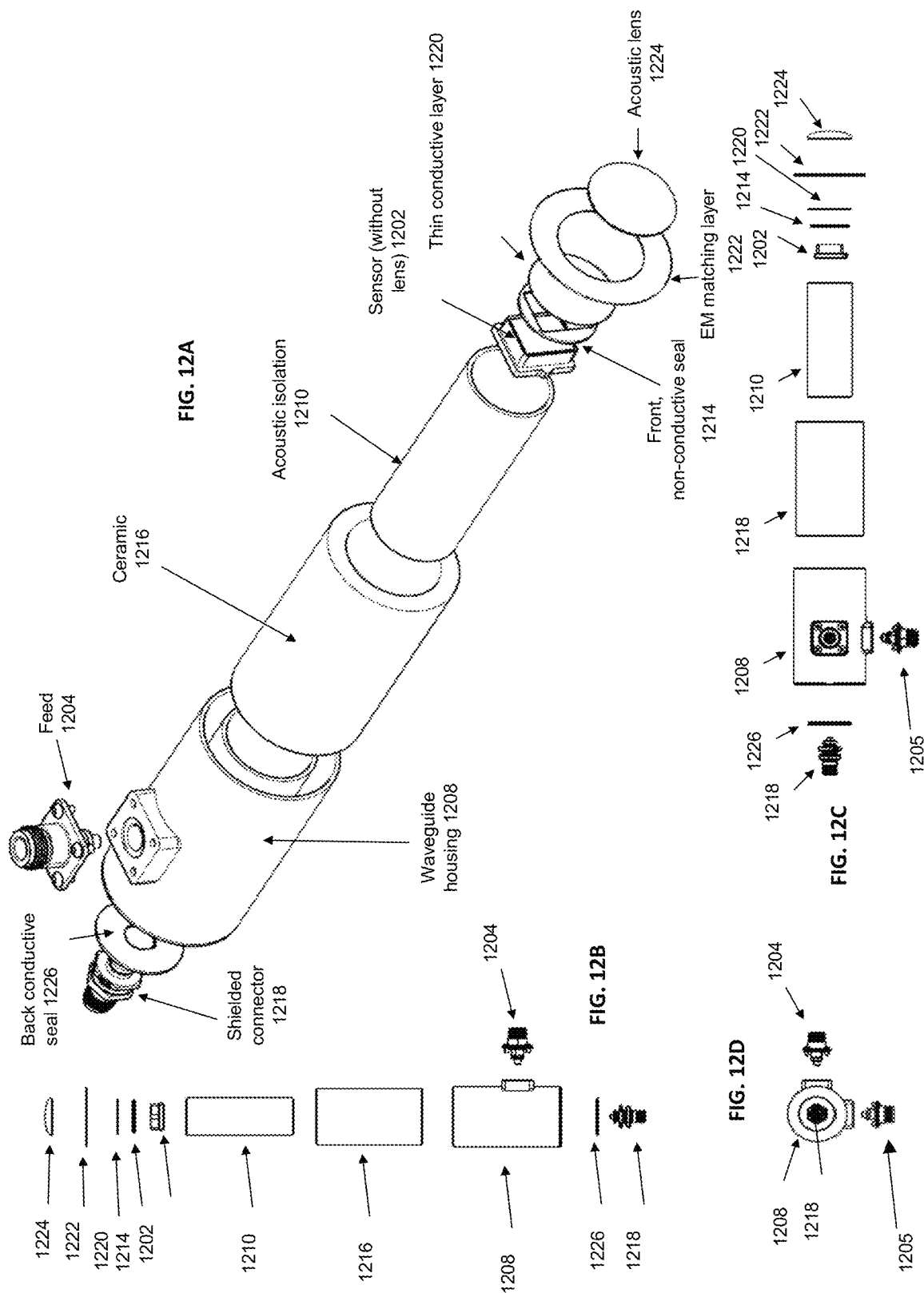

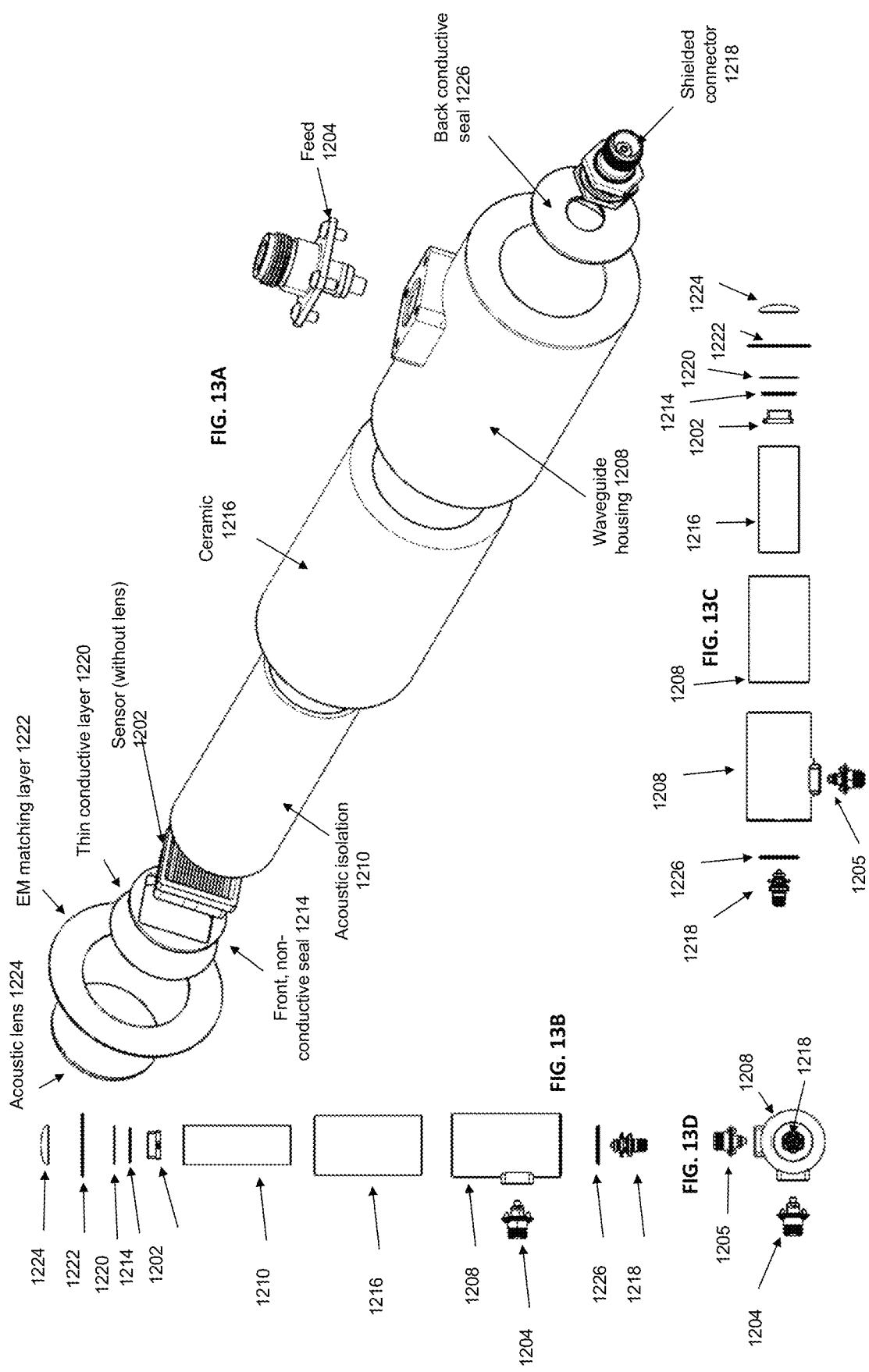

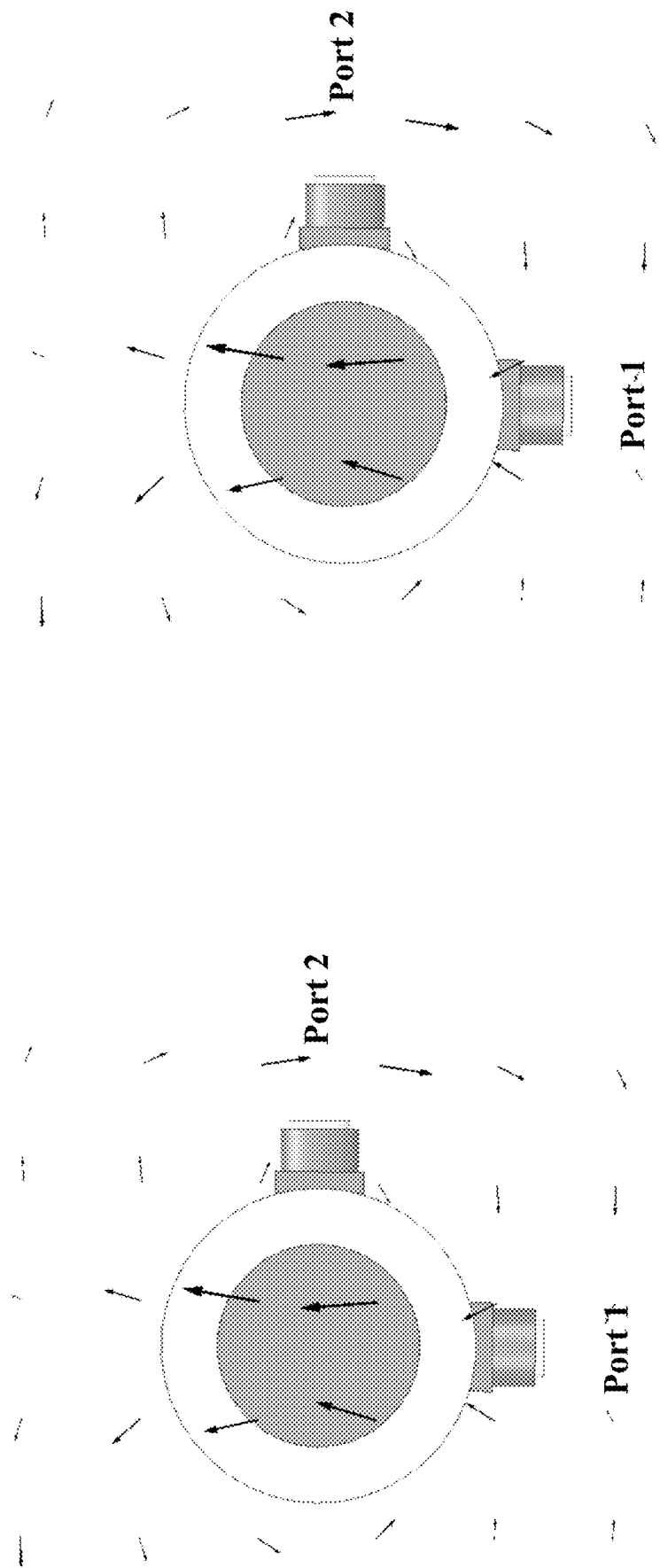
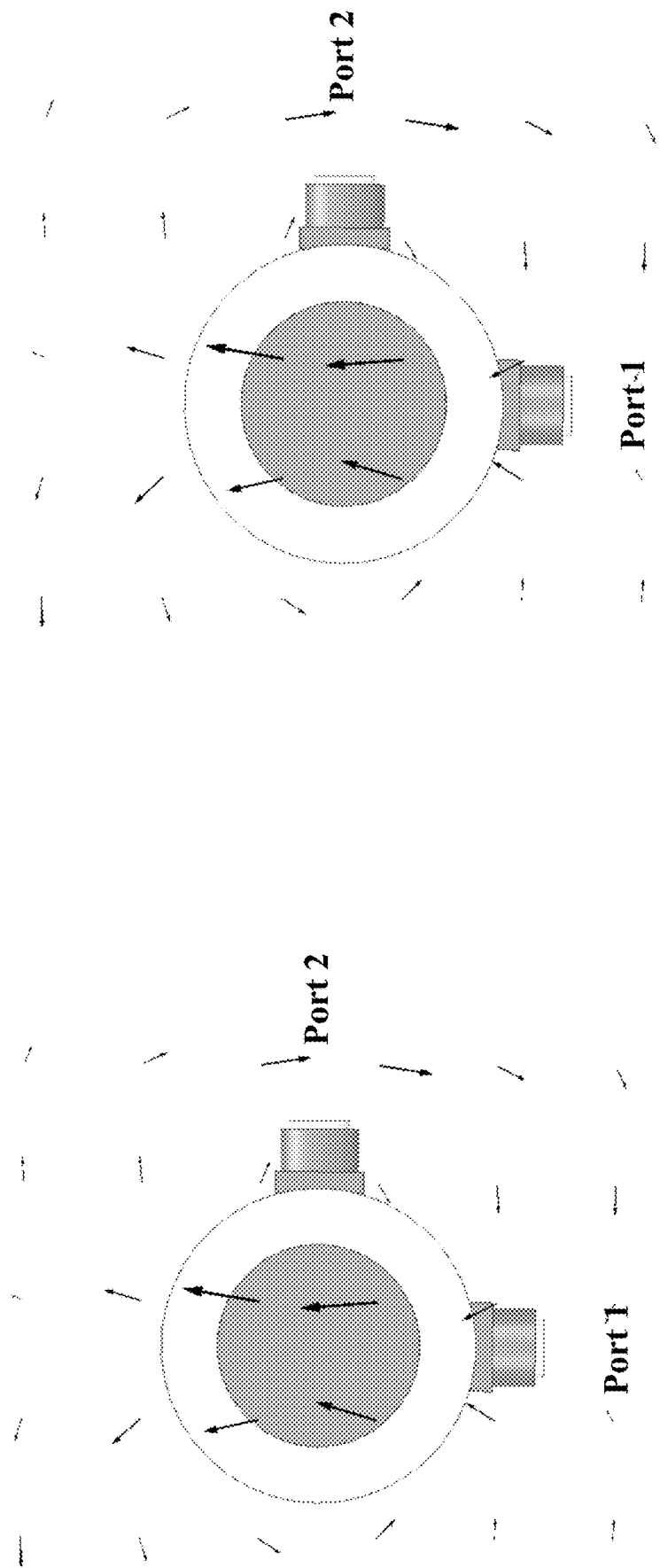
FIG. 19
FIG. 20

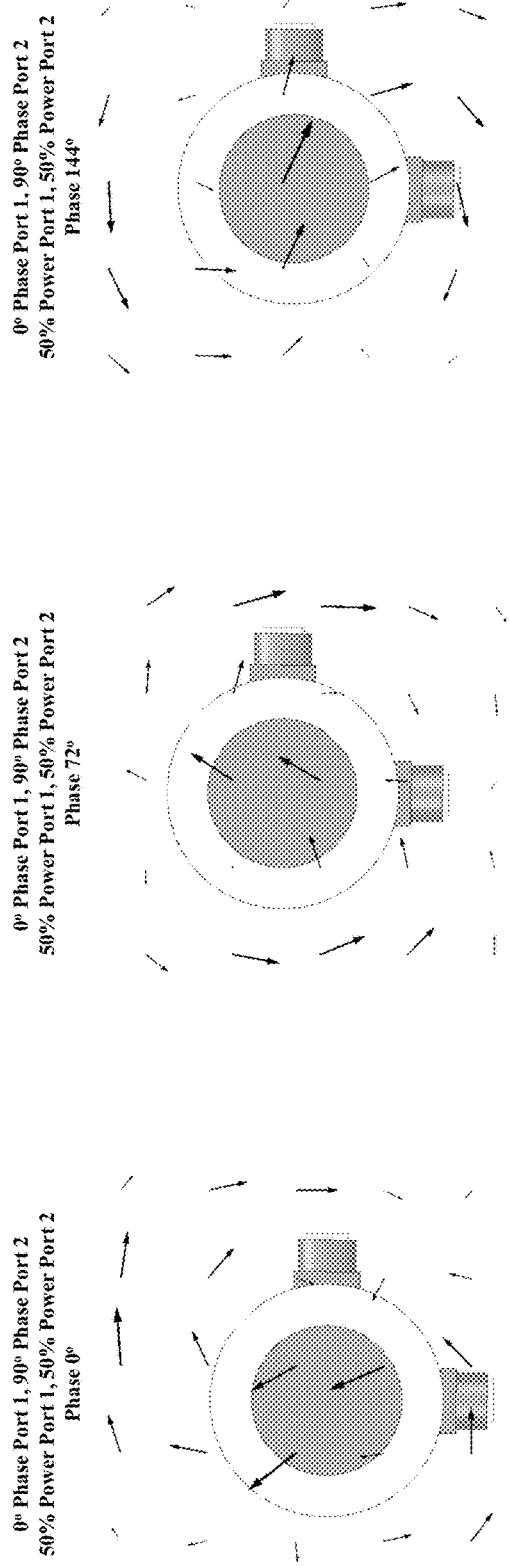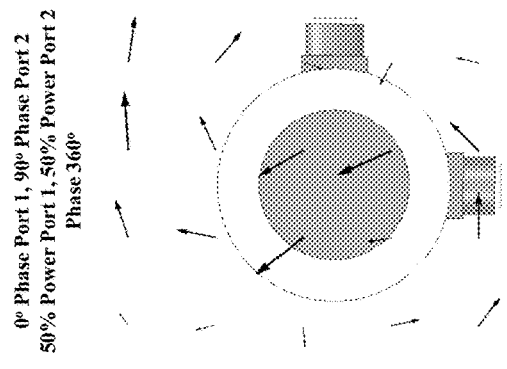

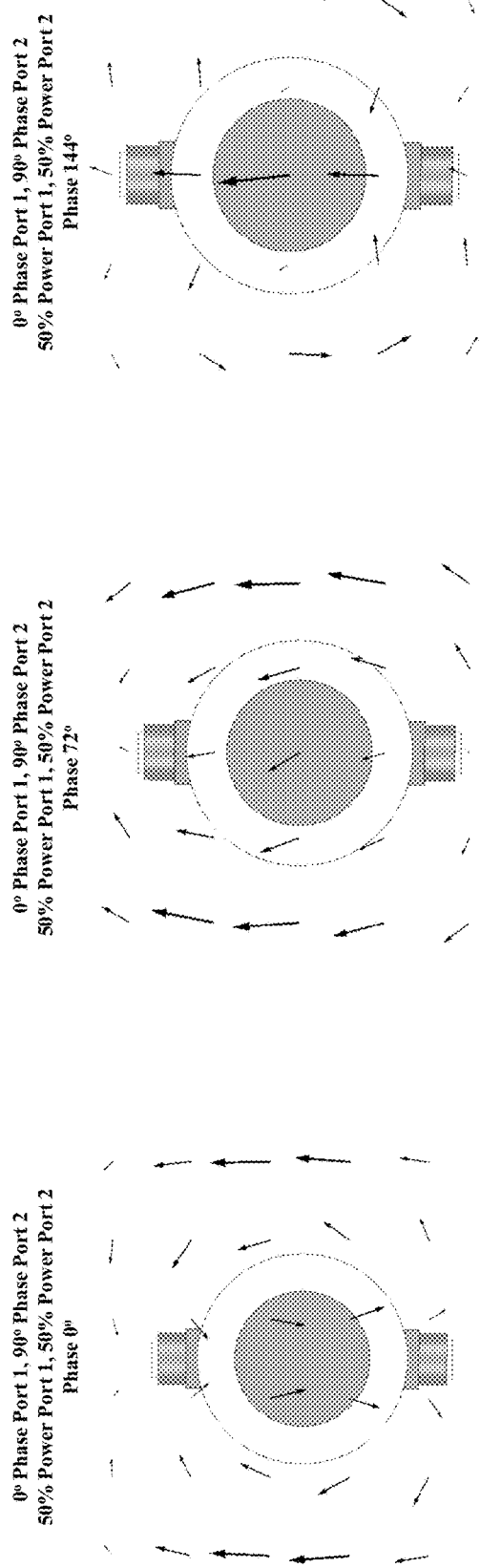
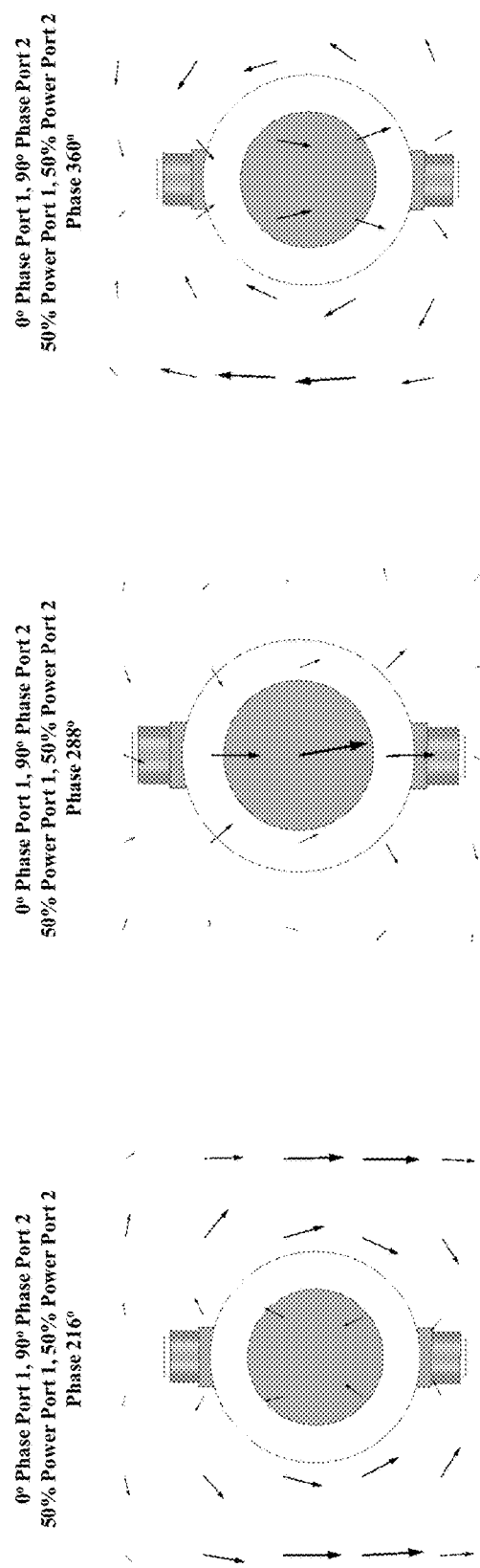

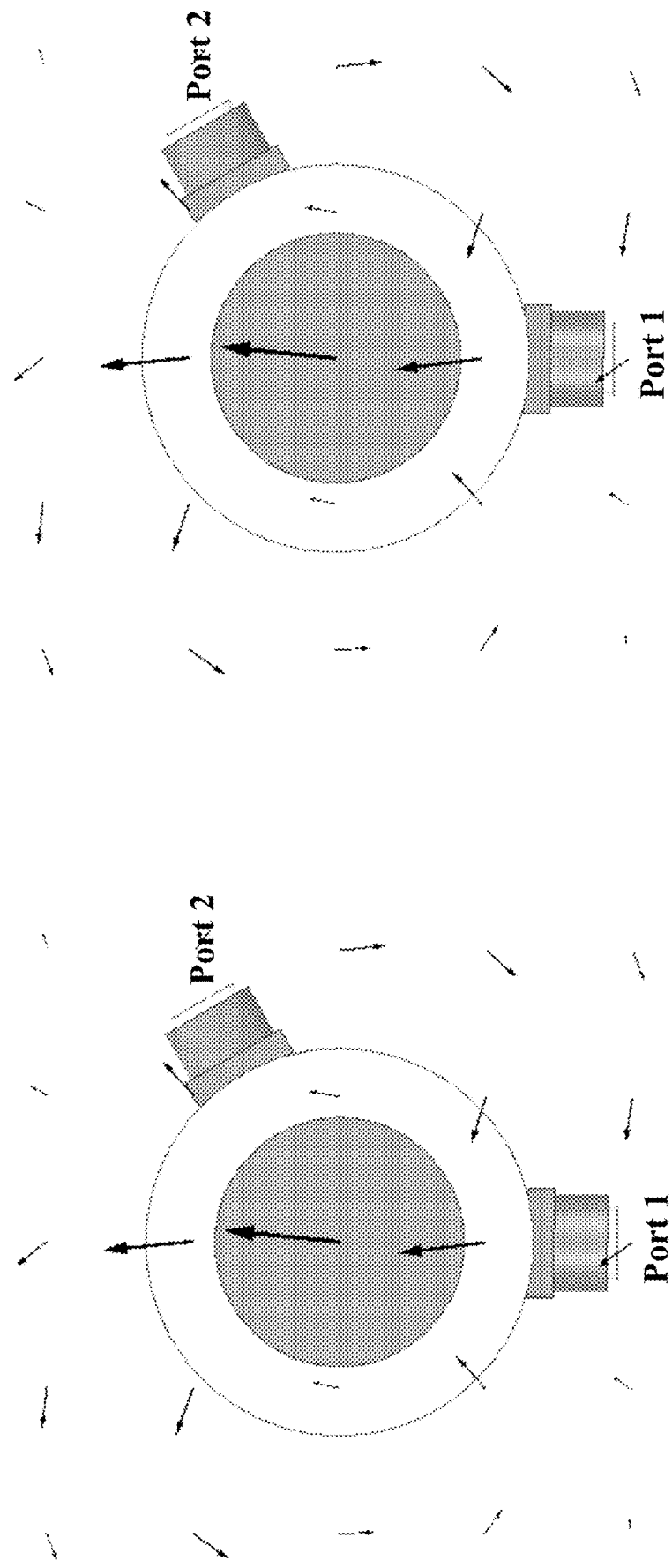

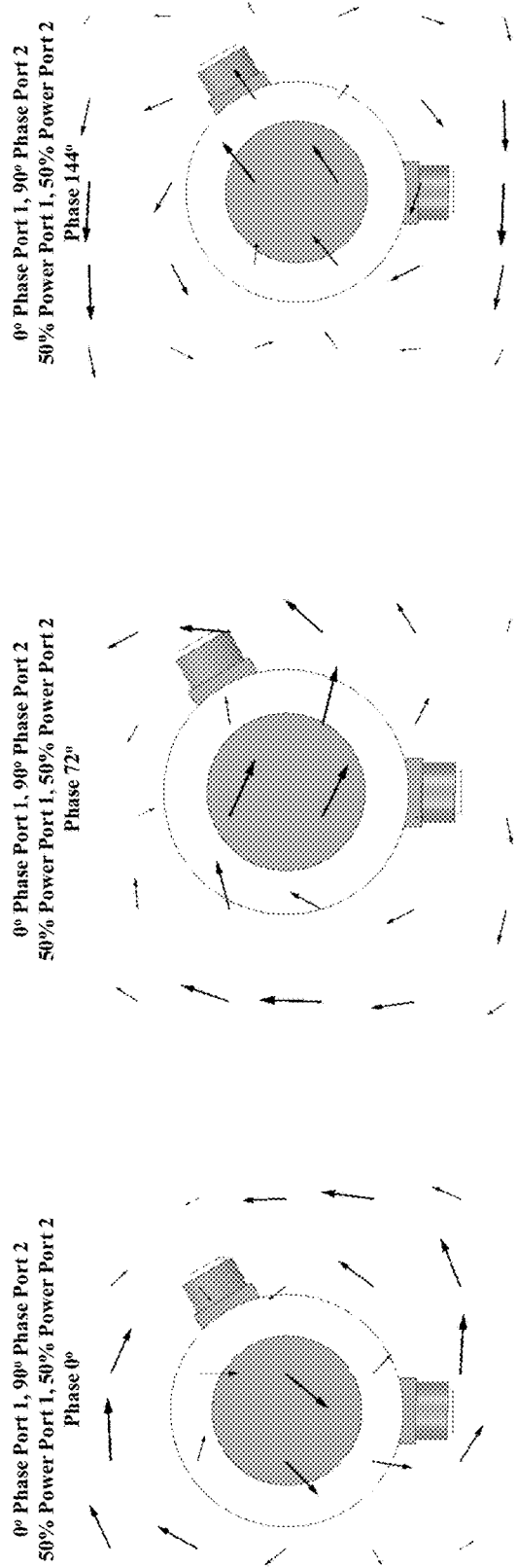

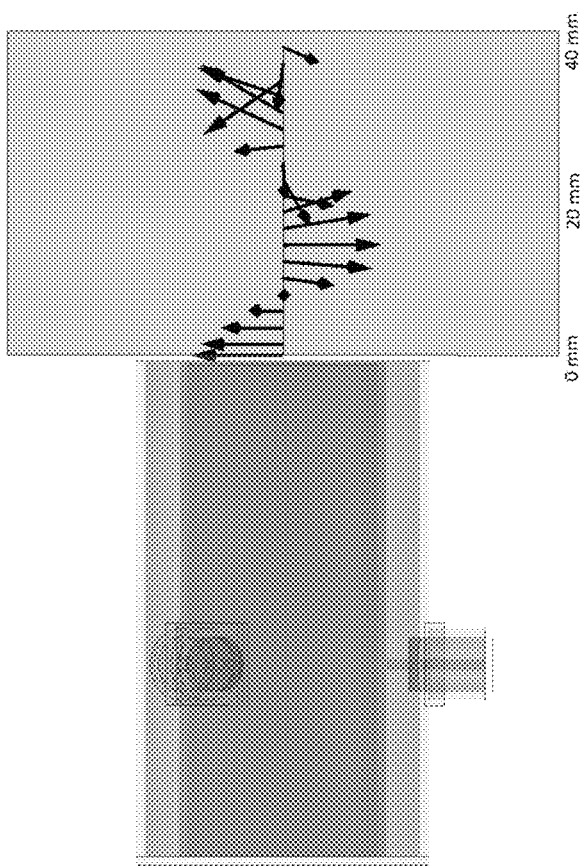
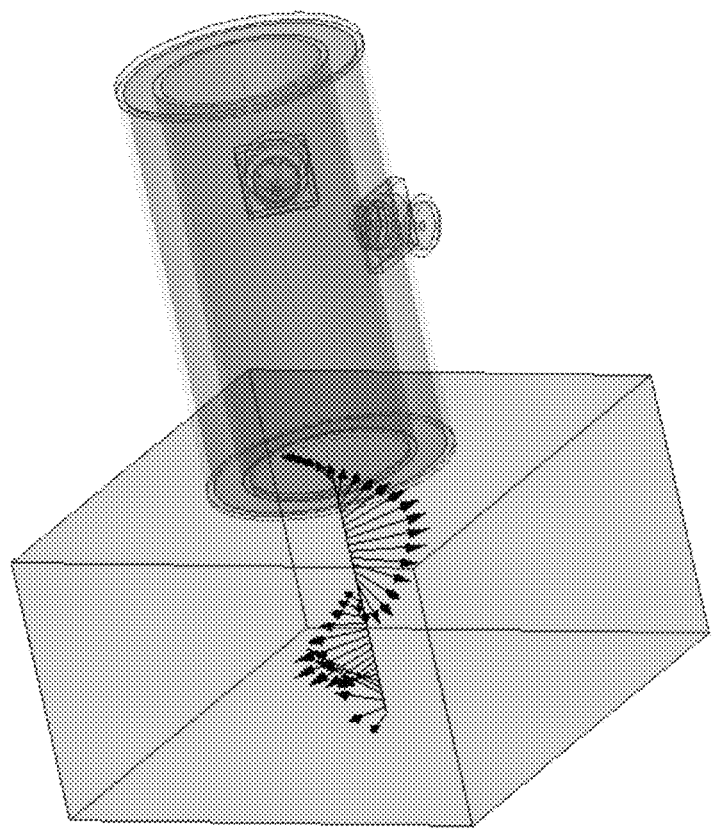
FIG. 61
FIG. 60

THERMOACOUSTIC MEASUREMENT PROBE

CROSS-REFERENCE TO RELATED APPLICATION

This application is a continuation-in-part of pending U.S. Non-Provisional application Ser. No. 17/946,700, filed on Sep. 16, 2022, which is herein incorporated by reference in its entirety.

TECHNICAL FIELD

The present disclosure enables a thermoacoustic measurement probe. In particular, the disclosure discussed structural configurations that enable a radio-frequency (RF) waveguide portion of a probe to surround a thermoacoustic transducer portion in a sleeve configuration and enable polarization of RF energy configured to emanate from the RF energy waveguide portion.

BACKGROUND

In high frequency systems, it is common to employ waveguides to guide electromagnetic waves or sound with minimal loss of energy by restricting expansion of the electromagnetic waves propagating within the waveguides to one or two dimensions. Depending on the nature of the electromagnetic waves to be propagated, the waveguides may take different forms. Also, in many instances, filters are employed to allow electromagnetic waves at some frequencies to pass and travel along the waveguides, while rejecting electromagnetic waves at other frequencies. One example is hollow, open-ended conductive waveguides, which are often employed for directing radio frequency (RF) waves. In some instances, to provide the desired filtering these hollow metal waveguides are fitted with a solid insert formed of high dielectric constant material.

Waveguides such as those described above have been employed in thermoacoustic imaging systems. Thermoacoustic imaging is an imaging modality that provides information relating to the thermoelastic properties of tissue. Thermoacoustic imaging uses short pulses of electromagnetic energy, such as RF pulses, directed into a medium to heat absorbing features within the medium rapidly, which in turn induces acoustic pressure waves that are detected using acoustic receivers such as one or more thermoacoustic or ultrasound transducer arrays. The detected acoustic pressure waves are analyzed through signal processing, and processed for presentation as thermoacoustic images that an operator can interpret.

In order to direct RF pulses into the medium during thermoacoustic imaging, an RF applicator employing a waveguide is coupled to tissue adjacent to a region of interest (ROI) within the medium to be imaged. Sub-optimal coupling of the RF applicator to the tissue may cause issues such as inefficient energy transfer, reduced heating rates, reduced signal intensity, non-uniform energy deposition, tissue hotspots, tissue overheating, RF power supply damage, and poor image quality. Factors that lead to sub-optimal coupling of the RF applicator to the tissue include variability in the medium's size, the size of tissue within the medium, the geometry of tissue within the medium, the composition of tissue within the medium, etc.

In a thermoacoustic probe, an RF applicator or RF antenna are used for transmitting RF energy into the medium of interest, and an acoustic receiver is used to pick up the resulting thermoacoustic waves. It is common to configure the RF applicator and acoustic receiver side-by-side, integrated into a single handheld probe.

The side-by-side configuration may result in lower thermoacoustic signal strength, thereby reducing the effectiveness of thermoacoustic measurements. This is because the signal strength and extent of the imageable region are dependent on the extent of overlap between the RF applicator beam and the acoustic receiver's directivity pattern.

Another disadvantage of a side-by-side configuration for a thermoacoustic probe is that RF interference from the RF applicator may also adversely affect signal quality.

A third disadvantage of a side-by-side configuration for a thermoacoustic probe may be that spurious acoustic signals, such as an RF applicator plane wave, are stronger and are detrimental to acoustic signal fidelity.

In a side-by-side configuration, one proposed solution is to tilt the acoustic receiver in relation to RF applicator. This approach can allow for better overlap, but only a certain depth. Unfortunately, this will not improve RFI or reduce a large plane-wave artifact (unwanted signal noise) that occurs.

Another proposed solution is to separate the receiver and applicator into two different devices that can increase signal strength and reduce artifacts. Unfortunately, this approach introduces multiple complications and higher variability, as now an operator needs to manipulate two devices simultaneously, which represents a massive obstruction to the standard of care clinical workflow. In a thermoacoustic probe, an applicator or antenna are used for transmitting RF energy into the medium of interest and an acoustic receiver is used to pick up the resulting thermoacoustic waves.

The thermoacoustic signal response can be dependent on the polarization of the RF energy that is incident in the tissue of interest. For example, structures such as blood vessels will generate a stronger thermoacoustic response if the polarization is parallel to the vessel.

Physically changing the orientation of the RF Applicator can change the polarization in the tissue, but this can be imprecise and non-repeatable. Hence, this is not a good solution.

It is difficult and time-consuming to do a high resolution sweep of polarization. So, this is not a good solution either.

Hence, there is a need to develop a novel structural thermoacoustic probe configuration that overcomes the limitations inherent in a side-by-side thermoacoustic probe configuration and also enables RF energy polarization.

SUMMARY

In one embodiment, thermoacoustic measurement probe comprises an open-ended hollow radio-frequency (RF) waveguide; individual RF feeds positioned within the open-ended hollow RF waveguide, wherein each individual RF feed is configured to provide RF energy at a different phase; and a thermoacoustic transducer; wherein the open-ended hollow RF waveguide, in the form of a sleeve, surrounds and is mechanically joined to the thermoacoustic transducer.

The open-ended hollow RF waveguide, in the form of a sleeve, may surround and be mechanically joined to the thermoacoustic transducer via insulation that protects the thermoacoustic transducer from acoustic and electrical interference emanating from the open-ended hollow RF waveguide.

The thermoacoustic transducer and open-ended hollow RF waveguide may form a circular cross-sectional shape.

The thermoacoustic transducer and open-ended hollow RF waveguide may form an elliptical cross-sectional shape.

A sensor of the thermoacoustic transducer may have a circular cross-sectional shape.

A sensor of the thermoacoustic transducer may have an elliptical cross-sectional shape.

A sensor of the thermoacoustic transducer may have a rectangular cross-sectional shape.

An end of a sensor of the thermoacoustic transducer may have a conical shape.

In another embodiment, a thermoacoustic measurement probe may comprise a radio-frequency (RF) waveguide having a cavity; individual RF feeds positioned within the RF waveguide, wherein each individual RF feed is configured to provide RF energy at a different phase; and a thermoacoustic transducer positioned in the cavity of the RF waveguide.

The cavity of the RF waveguide may have a circular cross-sectional shape.

The cavity of the RF waveguide may have an elliptical cross-sectional shape.

The cavity of the RF waveguide may have a rectangular cross-sectional shape.

A sensor of the thermoacoustic transducer may have a circular cross-sectional shape.

A sensor of the thermoacoustic transducer may have an elliptical cross-sectional shape.

A sensor of the thermoacoustic transducer may have a rectangular cross-sectional shape.

A sensor of the thermoacoustic transducer may have a conical shape.

A ceramic may be positioned in the cavity.

An acoustic isolation may be positioned in the ceramic.

The thermoacoustic measurement probe may comprise an RF feed coupled to the RF waveguide, and a connector coupled to the thermoacoustic transducer via an opening in the RF waveguide.

In yet another embodiment, a thermoacoustic measurement probe may comprise a cylindrical radio-frequency (RF) waveguide housing; individual RF feeds positioned within the RF waveguide housing, wherein each individual RF feed is configured to provide RF energy at a different phase; a cylindrical ceramic inside the cylindrical RF waveguide housing; a cylindrical acoustic isolation inside of the cylindrical ceramic; and a thermoacoustic sensor at an end of the cylindrical acoustic isolation.

In a separate embodiment, there are two individual RF feeds and they are located at 180 degrees relative to each other within the open-ended hollow RF waveguide.

In a separate embodiment, there are two individual RF feeds and they are located at 90 degrees relative to each other within the open-ended hollow RF waveguide.

In one embodiment, a thermoacoustic measurement probe may comprise an open-ended hollow radio-frequency (RF) waveguide; at least two RF feeds positioned within the open-ended hollow RF waveguide, wherein each RF feed is configured to provide RF energy; and a thermoacoustic transducer, wherein the open-ended hollow RF waveguide, in the form of a sleeve, surrounds and is mechanically joined to the thermoacoustic transducer.

The at least two RF feeds may be located at 180 degrees, 120 degrees, or 90 degrees relative to each other within the open-ended hollow RF waveguide.

The at least two RF feeds may comprise a first RF feed having a first phase and a second RF feed having a second phase different from the first phase.

The at least two RF feeds may comprise a first RF feed at a first power level and a second RF feed at a second power level different from the first power level. The at least two RF feeds may comprise a first RF feed and a second RF feed at the same power level.

In another embodiment, a thermoacoustic measurement probe may comprise a radio-frequency (RF) waveguide having a cavity; individual RF feeds positioned within the RF waveguide, wherein each individual RF feed is configured to provide RF energy at a different phase; and a thermoacoustic transducer positioned in the cavity of the RF waveguide.

The two individual RF feeds may be located at 180 degrees, 120 degrees, or 90 degrees relative to each other within the open-ended hollow RF waveguide.

The two individual RF feeds may comprise a first RF feed having a first phase and a second RF feed having a second phase completely out of phase from the first phase.

The two individual RF feeds may comprise a first RF feed at a first power level and a second RF feed at a second power level different from the first power level. The two individual RF feeds may comprise a first RF feed and a second RF feed at the same power level.

In yet another embodiment, a thermoacoustic measurement probe may comprise a cylindrical radio-frequency (RF) waveguide housing; a plurality of RF feeds positioned within the RF waveguide housing, wherein each RF feed is configured to provide RF energy; a cylindrical ceramic inside the cylindrical RF waveguide housing; a cylindrical acoustic isolation inside of the cylindrical ceramic; and a thermoacoustic sensor at an end of the cylindrical acoustic isolation.

The plurality of RF feeds may be located at 180 degrees, 120 degrees, or 90 degrees relative to each other within the cylindrical RF waveguide housing.

The plurality of RF feeds are located at 90 degrees relative to each other within the cylindrical RF waveguide housing.

Each RF feed of the plurality of RF feeds may provide RF energy at a different phase.

The plurality of RF feeds may comprise a first RF feed at a first power level and a second RF feed at a second power level different from the first power level. The plurality of RF feeds may comprise a first RF feed and a second RF feed at the same power level.

In various embodiments, each said RF feed comprises an axis and said RF feeds have either parallel or non-parallel axes.

It should be appreciated that this summary is provided to introduce a selection of concepts in a simplified form that are further described below in the detailed description. This summary is not intended to be used to limit the scope of the claimed subject matter.

BRIEF DESCRIPTION OF THE DRAWINGS

Embodiments will now be described more fully with reference to the accompanying drawings in which:

FIG. 7A is a front view of a third RF applicator and acoustic receiver sleeve configuration, according to an embodiment.

FIG. 7B is a perspective view of the third RF applicator and acoustic receiver sleeve configuration, according to an embodiment.

FIG. 7C is a side view of the third RF applicator and acoustic receiver sleeve configuration, according to an embodiment.

FIG. 7D is a top view of the third applicator and acoustic receiver sleeve configuration, according to an embodiment.

FIG. 10A is an exploded isometric view of a sixth RF applicator and acoustic receiver sleeve configuration, according to an embodiment.

FIG. 10B is an exploded side view of the sixth RF applicator and acoustic receiver sleeve configuration, according to an embodiment.

FIG. 10C is an exploded top view of the sixth RF applicator and acoustic receiver sleeve configuration, according to an embodiment.

FIG. 10D is an exploded side view of the sixth RF applicator and acoustic receiver sleeve configuration, according to an embodiment.

FIG. 11A is an alternative exploded isometric view of the sixth RF applicator and acoustic receiver sleeve configuration, according to an embodiment.

FIG. 11B is an alternative exploded side view of the sixth RF applicator and acoustic receiver sleeve configuration, according to an embodiment.

FIG. 11C is an alternative exploded top view of the sixth RF applicator and acoustic receiver sleeve configuration, according to an embodiment.

FIG. 11D is an alternative exploded side view of the sixth RF applicator and acoustic receiver sleeve configuration, according to an embodiment.

FIG. 12A is an exploded isometric view of a seventh RF applicator and acoustic receiver sleeve configuration, according to an embodiment.

FIG. 12B is an exploded side view of the seventh RF applicator and acoustic receiver sleeve configuration, according to an embodiment.

FIG. 12C is an exploded top view of the seventh RF applicator and acoustic receiver sleeve configuration, according to an embodiment.

FIG. 12D is an exploded side view of the seventh RF applicator and acoustic receiver sleeve configuration, according to an embodiment.

FIG. 13A is an alternative exploded isometric view of the seventh RF applicator and acoustic receiver sleeve configuration, according to an embodiment.

FIG. 13B is an alternative exploded side view of the seventh RF applicator and acoustic receiver sleeve configuration, according to an embodiment.

FIG. 13C is an alternative exploded top view of the seventh RF applicator and acoustic receiver sleeve configuration, according to an embodiment.

FIG. 13D is an alternative exploded side view of the seventh RF applicator and acoustic receiver sleeve configuration, according to an embodiment.

FIG. 19 shows a side-view of electric field polarization with two feeds at 90 degrees relative to each other, according to an embodiment.

FIG. 20 shows a side-view of electric field polarization with two feeds at 90 degrees relative to each other, according to an embodiment.

FIG. 29A-29F show a side-view of electric field polarization with two feeds at 90 degrees relative to each other at six different points in a cycle, according to an embodiment.

FIG. 44A-44F show a side-view of electric field polarization with two feeds at 180 degrees relative to each other at six different points in a cycle, according to an embodiment.

FIG. 55 shows a side-view of electric field polarization with two feeds at 120 degrees relative to each other, according to an embodiment.

FIG. 56 shows a side-view of electric field polarization with two feeds at 120 degrees relative to each other, according to an embodiment.

FIG. 59A-59F show a side-view of electric field polarization with two feeds at 120 degrees relative to each other at six different points in a cycle, according to an embodiment.

FIG. 60 shows an isometric view of electric field polarization with two feeds at 120 degrees relative to each other at a varying distance into tissue, according to an embodiment.

FIG. 61 shows a side-view of electric field polarization with two feeds at 120 degrees relative to each other at a varying distance into tissue, according to an embodiment.

DETAILED DESCRIPTION

Figure 1:
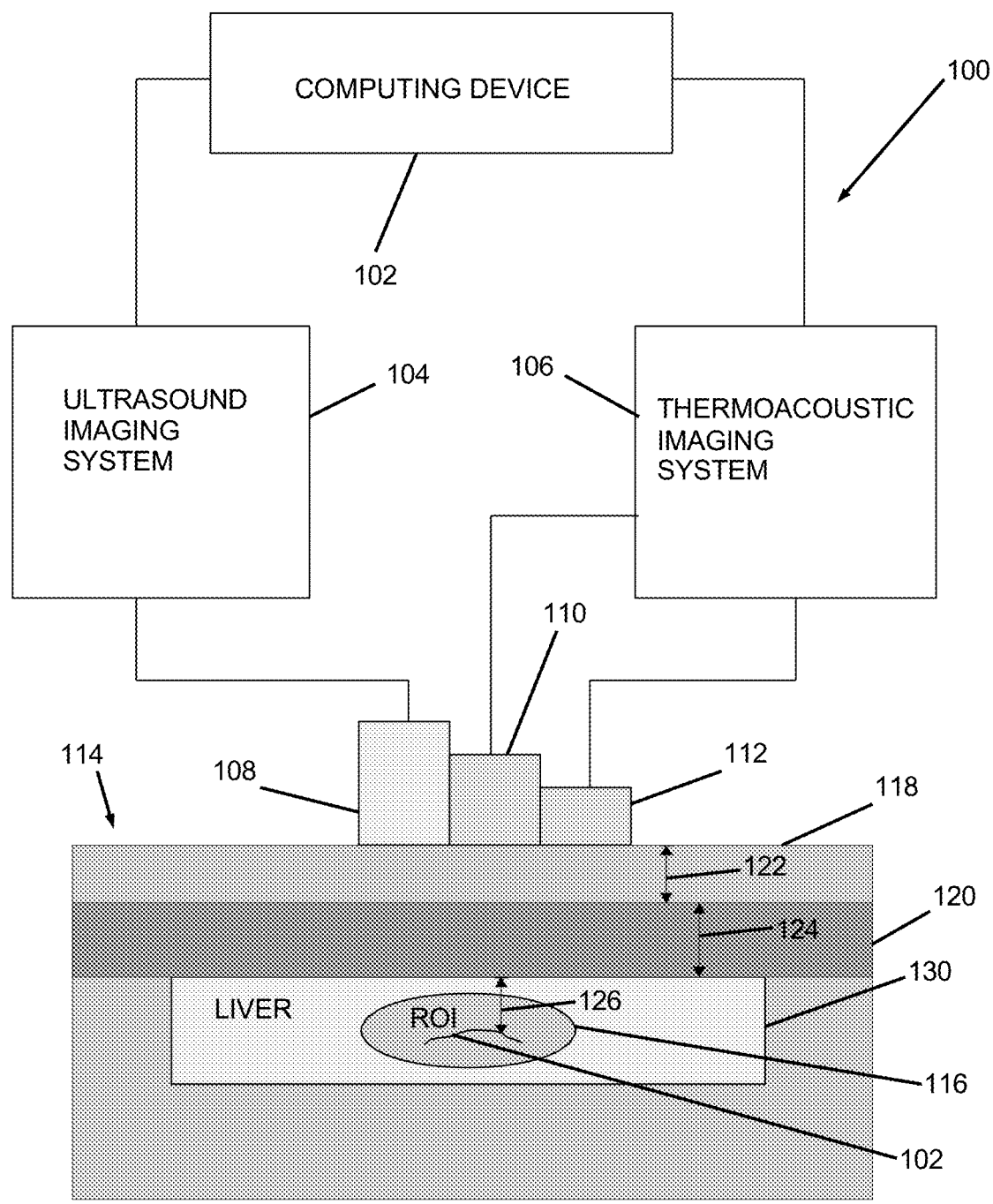
FIG. 1 is a block diagram of a thermoacoustic system, according to an embodiment.

Embodiments herein describe a thermoacoustic measurement probe having an RF waveguide that surrounds a thermoacoustic transducer, and a housing of the thermoacoustic measurement probe contains both the RF waveguide and the thermoacoustic transducer.

Embodiments herein describe an improved method and system. Rather than utilizing an open-ended RF waveguide and a separate acoustic receiver, the embodiments discussed herein may utilize an open-ended hollow RF waveguide, wherein the hollow portion is a cavity configured for an acoustic receiver and any additional electronics to be mounted within that cavity. This configuration may allow the mechanical installation of the acoustic receiver (thermoacoustic transducer) and any additional electronics inside the hollow cavity. The open-ended RF waveguide may be configured in a form of a sleeve, which may partially or entirely surround the acoustic receiver. The RF waveguide may also be mechanically joined to the acoustic receiver.

For the purposes of this disclosure, the terms "feed" and "port" are used interchangeably.

The use of a hollow RF waveguide is not conventionally used with a component, such as a thermoacoustic transducer, in a hollow portion, because a component could affect the field and operation of the RF waveguide. In the embodiments described herein, the RF waveguide may be configured with a null region in the hollow portion.

An unexpected result of placing the acoustic receiver inside the hollow cavity of an open-ended hollow RF waveguide is that it allows for maximal overlap between the RF beam and the acoustic receiver's directivity pattern.

Another unexpected result of utilizing an open-ended hollow RF waveguide is a very low electromagnetic field inside the hollow cavity. Placing the acoustic receiver inside the cavity (within the sleeve) reduces RF interferences significantly.

Another unexpected result is that the hollow RF waveguide has a highly divergent beam pattern near the RF waveguide. This, in turn, generates a diverging applicator plane wave which quickly disperses.

An unexpected result is that the hollow RF waveguide allows for smaller overall thermoacoustic measurement probe dimensions because the electronics and acoustic receiver can be placed inside the hollow cavity.

The cross-sectional shape of the hollow portion of the open-ended hollow RF waveguide can be any shape, including circular, elliptical, non-concentric tube, or tapered tube. The open-ended portion may contain a ceramic fill. In one embodiment, metal fins may be included in the ceramic fill or mounted on the RF waveguide to increase the frequency bandwidth over which the RF applicator can efficiently operate.

In one embodiment, the present disclosure enables an RF Applicator with electronic real-time adjustable polarization, including circular polarization. The RF applicator has adjustable polarization by electronically changing the relative phase between two or more RF energy feeds located within the RF Applicator.

The RF applicator can quickly sweep through polarizations at a measurement location and the resulting thermoacoustic response can be quantified versus polarization.

Polarization of the RF applicator can be precisely and repeatedly controlled by the relative phase between the RF energy feeds.

Turning now to FIG. 1, an imaging system is shown and is generally identified by reference numeral 100. As can be seen, the imaging system 100 comprises a programmed computing device 102 communicatively coupled to an ultrasound imaging system 104 and to a thermoacoustic imaging system 106. The ultrasound imaging system 104 and thermoacoustic imaging system 106 are configured to obtain ultrasound image data and thermoacoustic image data, respectively, of a region of interest (ROI) 116.

The programmed computing device 102 in this embodiment may be a personal computer, server, or other suitable processing device comprising, for example, a processing unit comprising one or more processors, computer-readable system memory (volatile and/or non-volatile memory), other non-removable or removable computer-readable memory (e.g., a hard disk drive, RAM, ROM, EEPROM, CD-ROM, DVD, flash memory, etc.) and a system bus coupling the various computer components to the processing unit. The computing device 102 may also comprise networking capabilities using Ethernet, Wi-Fi, and/or another suitable network format to enable connection to shared or remote drives, one or more networked computers, or other networked devices. One or more input devices, such as a mouse and a keyboard (not shown) are coupled to the computing device 102 for receiving operator input. A display device (not shown), such as one or more computer screens or monitors, may be coupled to the computing device 102 for displaying one or more generated images that are based on ultrasound image data received from the ultrasound imaging system 104 and/or the thermoacoustic image data received from the thermoacoustic imaging system 106. The programmed computing device 102 executes program code stored on the computer-readable system memory and/or other non-removable or removable computer-readable memory and performs methods according to the program code, as described further below.

The ultrasound imaging system 104 comprises an acoustic receiver in the form of an ultrasound transducer 108 that houses one or more ultrasound transducer arrays configured to emit sound waves into the region of interest 116. Sound waves directed into the region of interest 116 echo off materials within the region of interest, with different materials reflecting varying degrees of sound. Echoes that are received by the one or more ultrasound transducer arrays of the ultrasound transducer 108 are processed by the ultrasound imaging system 104. The ultrasound imaging system 104 communicates ultrasound image data to the computing device 102 for further processing and for presentation on the display device as ultrasound images that an operator can interpret. In one embodiment, the ultrasound imaging system 104 utilizes B-mode ultrasound imaging techniques assuming a nominal speed of sound of 1,540 m/s. As ultrasound imaging systems are known in the art, further specifics of the ultrasound imaging system 104 will not be described further herein.

The thermoacoustic imaging system 106 comprises an acoustic receiver in the form of a thermoacoustic transducer 110. The thermoacoustic transducer 110 houses one or more thermoacoustic transducer arrays. As described herein, although shown as separate components in the schematic FIG. 1, a radio-frequency (RF) applicator (or waveguide) 112 may be housed, combined, or integrated with the thermoacoustic transducer 110. The RF applicator 112 is configured to emit short pulses of RF energy that are directed into the region of interest 116. In one embodiment, the RF applicator 112 has a frequency between about 10 Mhz and 100 GHz and has a pulse duration between about 0.1 nanoseconds and 10 microseconds. The RF applicator 112 emits RF energy pulses to materials or tissue within the region of interest 116 to induce acoustic pressure waves (thermoacoustic multi-polar signals) within the region of interest 116 that are detected by the thermoacoustic transducer 110. Acoustic pressure waves detected by the thermoacoustic transducer 110 are processed and communicated as thermoacoustic image data to the computing device 102 for further processing and presentation on the display device as thermoacoustic images that the operator can interpret.

The coordinate system of the one or more ultrasound transducer arrays of the ultrasound transducer 108 and the coordinate system of the one or more thermoacoustic transducer arrays of the thermoacoustic transducer 110 are mapped by the computing device 102 so that acquired ultrasound and thermoacoustic images can be registered. Alternatively, the thermoacoustic imaging system 106 may make use of the one or more ultrasound transducer arrays of the ultrasound transducer 108 by disconnecting the one or more ultrasound transducer arrays from the ultrasound transducer 108 and connecting the one or more ultrasound transducer arrays to the thermoacoustic transducer 110. As will be appreciated, by doing this coordinate mapping between the one or more ultrasound transducer arrays and the one or more thermoacoustic transducer arrays is not required.

In one embodiment (shown in FIG. 1), the region of interest 116 contains blood vessel 102 and is located within a liver 130 of a human or animal body (patient) 114. Patient 114 comprises a subcutaneous fat layer 118 and muscle layer 120 adjacent to liver 130. Distances shown: $d_f$ is the subcutaneous fat thickness of the patient 122, $d_m$ is the muscle thickness of the patient 124, $d_b$ is the distance from the boundary between the muscle and the liver to the center of the blood vessel 126.

Figure 2:
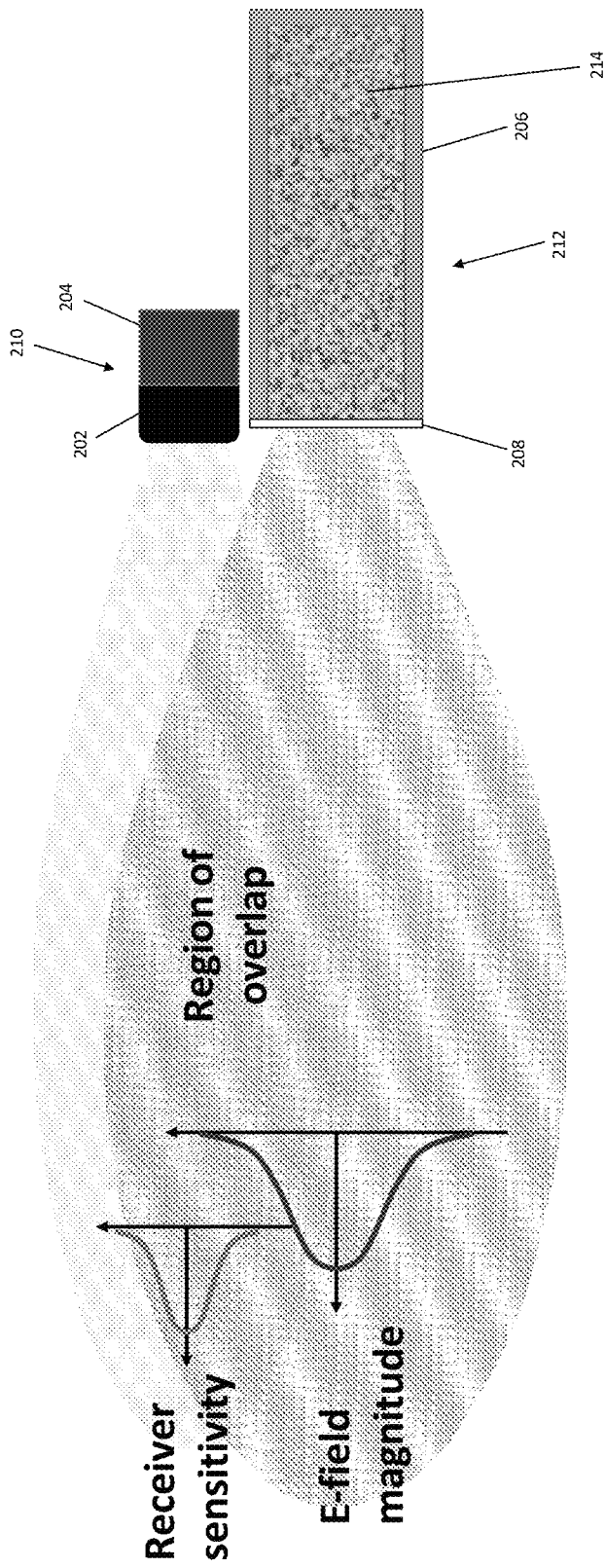
FIG. 2 is a cross-sectional side-view of an RF applicator and acoustic receiver side-by-side configuration, according to an embodiment.

FIG. 2 is a cross-sectional side-view of an RF applicator and acoustic receiver side-by-side configuration embodiment. Shown are thermoacoustic transducer 210 including thermoacoustic sensor 202 and thermoacoustic electronics 204, and RF applicator 212 including RF waveguide 206, RF matching layer 208, and RF applicator fill 214. In the side-by-side configuration of FIG. 2, an area/volume of an electric field with sufficient magnitude to generate a thermoacoustic signal and the area/volume of receiver sensitivity to detect and utilize a thermoacoustic signal have a small region of overlap. Hence, a thermoacoustic analysis occurs within this small region of overlap.

Figure 3:
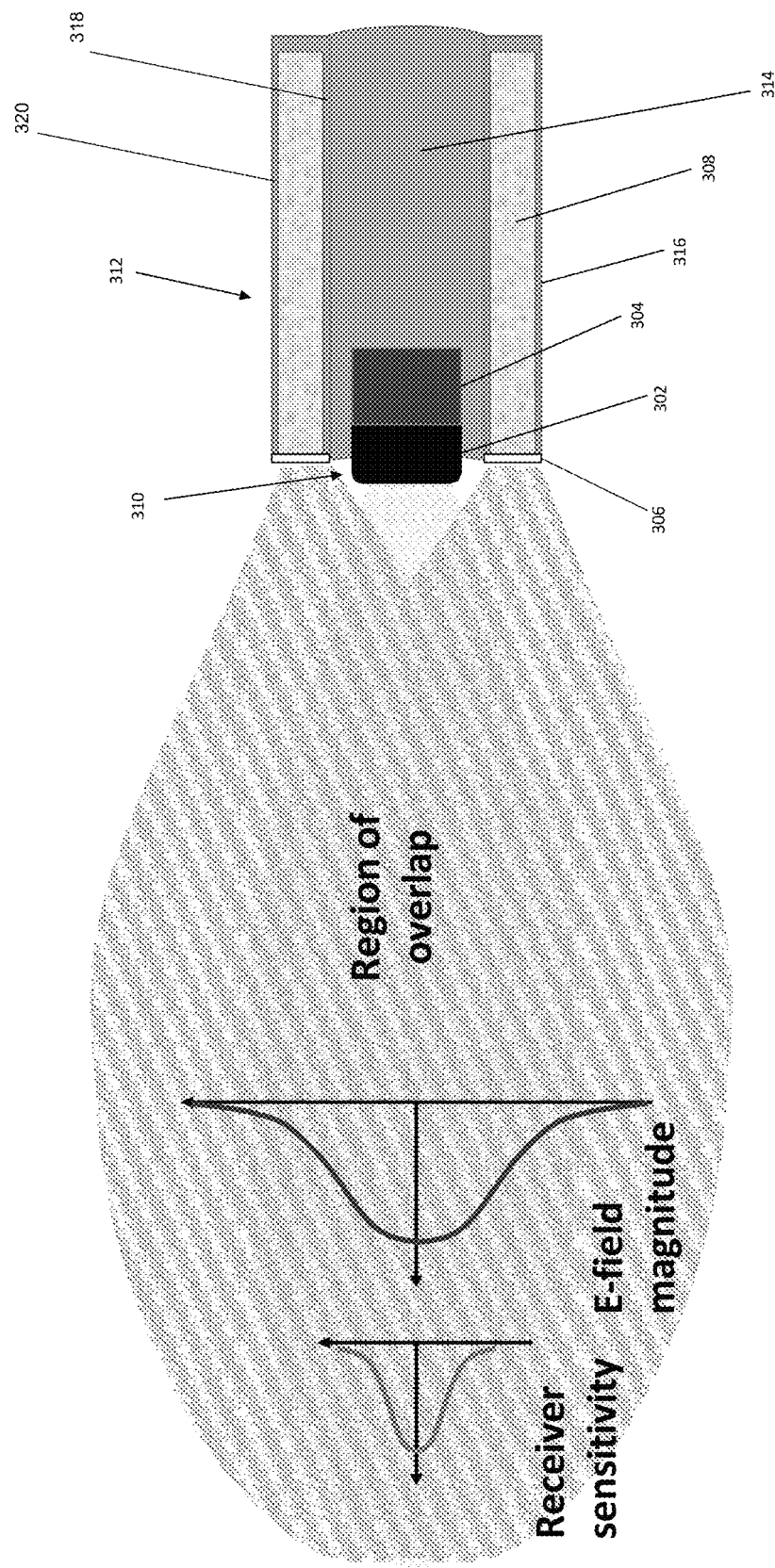
FIG. 3 is a cross-sectional side-view of an RF applicator and acoustic receiver sleeve configuration, according to an embodiment.

The thermoacoustic transducer may be configured to be housed within a cavity 314 formed by the RF applicator. In one example, FIG. 3 is a cross-sectional side-view of an RF applicator and acoustic receiver configuration. Shown are open-ended hollow RF applicator 312, open-ended hollow waveguide body 316, open-ended hollow waveguide matching layer 306, open-ended hollow waveguide fill 308, thermoacoustic transducer 310, thermoacoustic sensor 302, thermoacoustic electronics 304, and cavity 314 (which in one embodiment is filled with both acoustic and electromagnetic insulation). In this embodiment, the thermoacoustic transducer 310 is positioned within an interior region of the open-ended hollow RF applicator 312. In this configuration of FIG. 3, an area/volume of an electric field with sufficient magnitude to generate a thermoacoustic signal and the area/volume of receiver sensitivity to detect and utilize a thermoacoustic signal have a larger region of overlap as compared to FIG. 2.

In one embodiment, open-ended hollow waveguide fill 308 comprises the volume between cavity outer wall 318 and open-ended hollow waveguide body outer wall 320. Material used for the open-ended hollow waveguide fill 308 can be Strontium Titanate, Titanium Dioxide, Barium Strontium Titanate (BST). In one embodiment, the material used for the open-ended hollow waveguide fill 308 has a permittivity range of 10-250 relative real permittivity. In another embodiment, the material used for the open-ended hollow waveguide fill 308 has a Permittivity Loss Tangent from 0.00001 to 0.0050.

Figure 4:
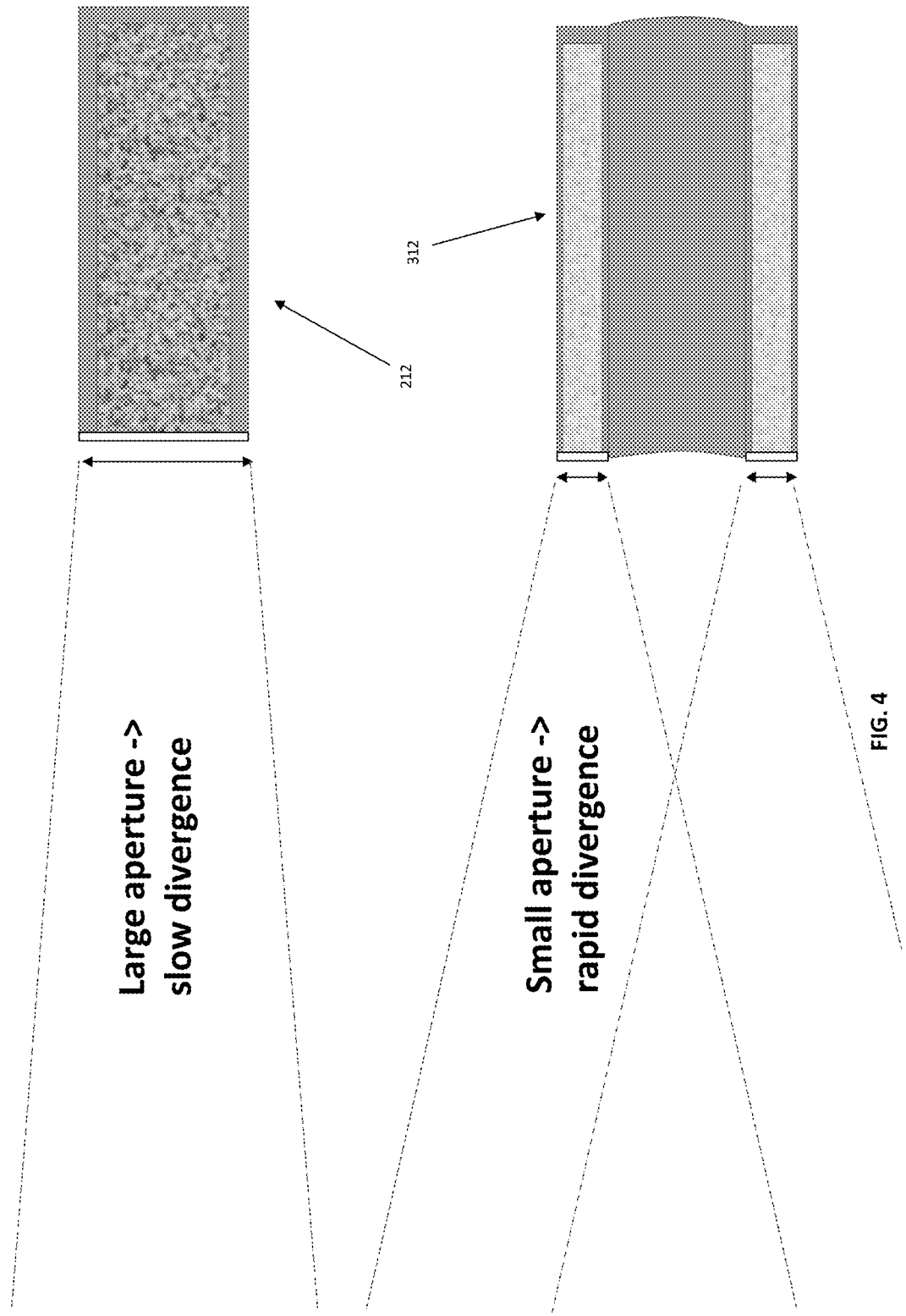
FIG. 4 is a signal divergence comparison between a standard RF applicator used in the prior art and the sleeve RF applicator of the present application.

FIG. 4 illustrates a signal divergence comparison between a conventional RF applicator shown in FIG. 2 and the RF applicator configuration shown in FIG. 3. RF applicator 212 is shown as a solid RF applicator with a large aperture and a slow divergence of RF energy. Open-ended hollow RF applicator 312 is shown with a small aperture where the RF energy is emitted and rapid divergence of RF energy. The divergence of RF energy is inversely proportional to the antenna aperture: the smaller the aperture, the larger the divergence angle, and vice versa. As shown in FIG. 4, the open-ended hollow RF applicator 312 has a smaller aperture, and this produces a larger divergence of the RF energy from the radiating surface of the applicator.

Figure 5A:
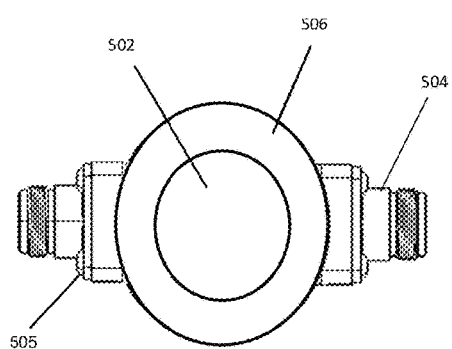
FIG. 5A is a front view of a first RF applicator and acoustic receiver sleeve configuration, according to an embodiment.
Figure 5B:
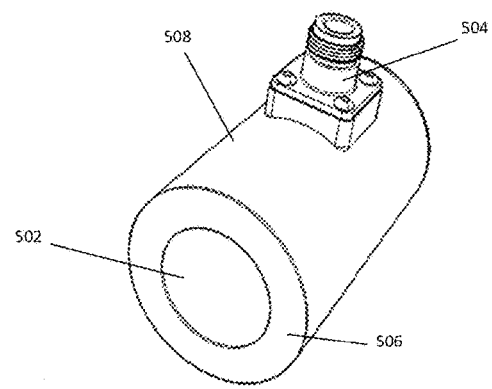
FIG. 5B is a perspective view of the first RF applicator and acoustic receiver sleeve configuration, according to an embodiment.
Figure 5C:
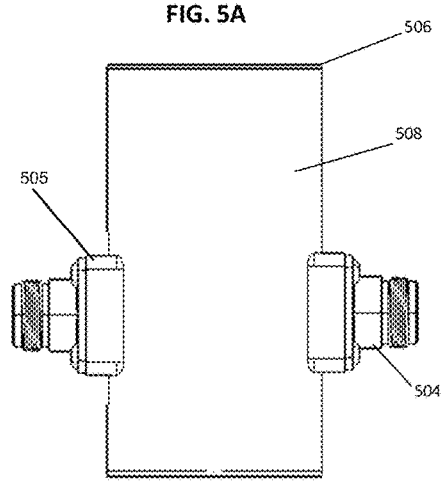
FIG. 5C is a side view of the first RF applicator and acoustic receiver sleeve configuration, according to an embodiment.
Figure 5D:
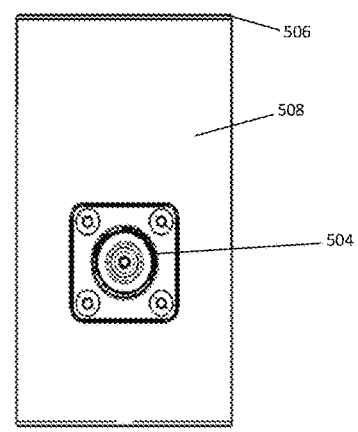
FIG. 5D is a top view of the first applicator and acoustic receiver sleeve configuration, according to an embodiment.

FIGS. 5A to 5D illustrate an RF applicator according to an embodiment. FIG. 5A is a front view of an RF applicator and acoustic receiver sleeve configuration embodiment. FIG. 5B is a perspective view of the RF applicator and acoustic receiver sleeve configuration embodiment. Shown are hollow cavity 502, open-ended hollow waveguide matching layer 506, open-ended hollow waveguide body 508, first RF energy feed 504, and second RF energy feed 505 rotated 180 degrees about the RF applicator from the first RF energy feed 504. FIG. 5C is a side view of the RF applicator and acoustic receiver sleeve configuration embodiment. FIG. 5D is a top view of the applicator and acoustic receiver sleeve configuration embodiment. In the illustrations of FIGS. 5A to 5D, the hollow cavity 502 is configured to receive an acoustic receiver (thermoacoustic transducer). The RF applicator may be considered an acoustic receiver sleeve because it is at least partially hollow and configured to house the acoustic receiver (not shown) in that opening. The acoustic receiver may fill all or a portion of the hollow cavity 502, and any portion of the hollow cavity 502 not filled by the acoustic receiver may be at least partially filled by another material, such as insulation.

As shown in examples of FIGS. 5A to 9D, an RF applicator and an acoustic receiver may have different shapes and configures. The RF applicator may be circular, elliptical, or other configuration having an open-ended portion (e.g., cavity) for receiving the acoustic receiver. The acoustic receiver may have a rectangular, circular, elliptical, or other shape cross-section, and may have a rectangular, spherical, conical, or other shape end. FIGS. 5A to 9D are meant to be examples of configurations and the potential configurations are not limited to these particular examples. The shape may be selected based on the desired application or manufacturing processes.

Figure 6A:
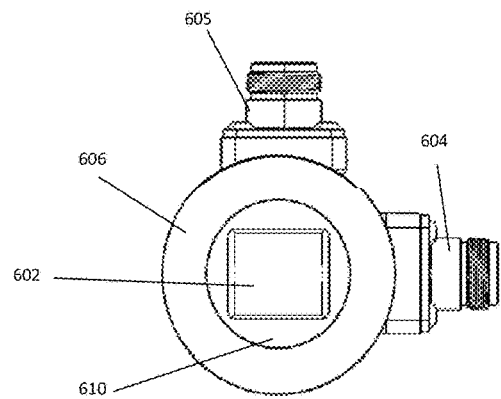
FIG. 6A is a front view of a second RF applicator and acoustic receiver sleeve configuration, according to an embodiment.
Figure 6B:
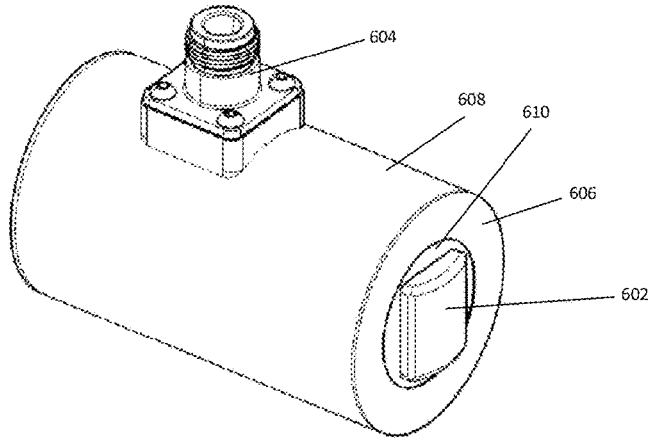
FIG. 6B is a perspective view of the second RF applicator and acoustic receiver sleeve configuration, according to an embodiment.
Figure 6C:
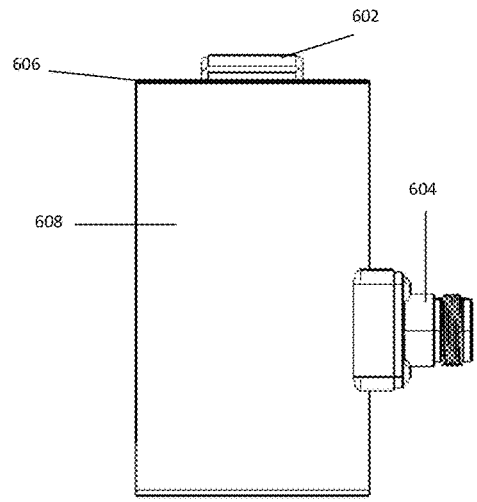
FIG. 6C is a side view of the second RF applicator and acoustic receiver sleeve configuration, according to an embodiment.
Figure 6D:
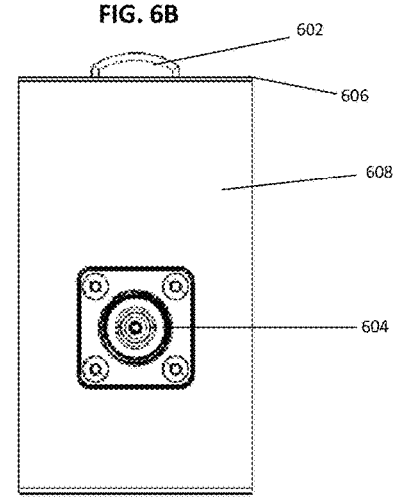
FIG. 6D is a top view of the second applicator and acoustic receiver sleeve configuration, according to an embodiment.

In one configuration, the acoustic receiver may have a rectangular shape and be positioned in an RF applicator, as shown in FIGS. 6A to 6D. FIG. 6A is a front view of a second RF applicator and acoustic receiver sleeve configuration embodiment. FIG. 6B is a perspective view of a second RF applicator and acoustic receiver sleeve configuration embodiment. Shown are open-ended hollow waveguide matching layer 606, open-ended hollow waveguide body 608, first RF energy feed 604, second RF energy feed 605 rotated 90 degrees about RF applicator from the first RF energy feed 604, insulation 610, and rectangular acoustic receiver 602 (with rectangular cross-section). FIG. 6C is a side view of a second RF applicator and acoustic receiver sleeve configuration embodiment. FIG. 6D is a top view of a second applicator and acoustic receiver sleeve configuration embodiment.

In another configuration, an acoustic receiver may have a conical shape and be positioned in an RF applicator, as shown in FIGS. 7A to 7D. FIG. 7A is a front view of a third RF applicator and acoustic receiver sleeve configuration embodiment. FIG. 7B is a perspective view of a third RF applicator and acoustic receiver sleeve configuration embodiment. Shown are open-ended hollow waveguide matching layer 706, open-ended hollow waveguide body 708, first RF energy feed 704, second RF energy feed 705 rotated 180 degrees about the RF applicator from the first RF energy feed 704, insulation 710, and conical acoustic receiver 702 (with circular cross-section). FIG. 7C is a side view of a third RF applicator and acoustic receiver sleeve configuration embodiment. FIG. 7D is a top view of a third applicator and acoustic receiver sleeve configuration embodiment.

Figure 8A:
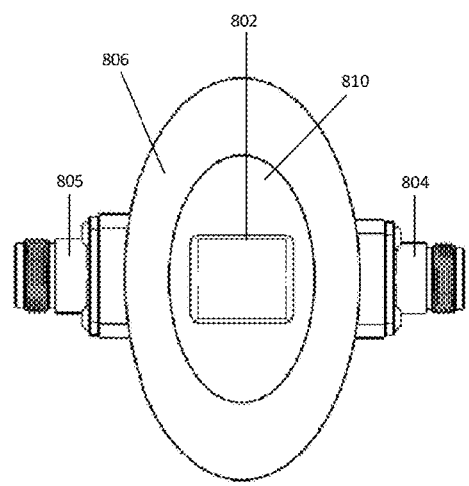
FIG. 8A is a front view of a fourth RF applicator and acoustic receiver sleeve configuration, according to an embodiment.
Figure 8B:
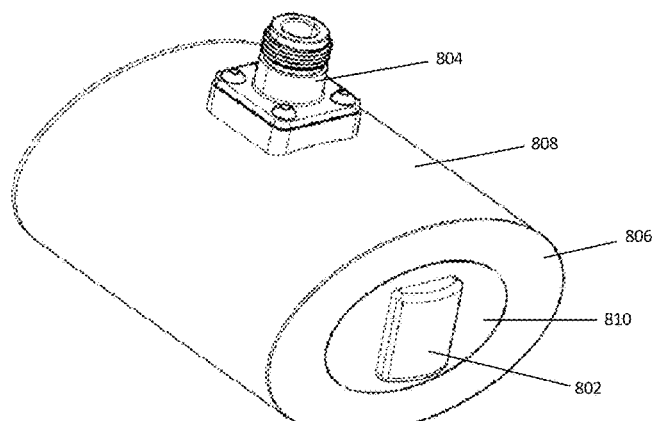
FIG. 8B is a perspective view of the fourth RF applicator and acoustic receiver sleeve configuration, according to an embodiment.
Figure 8C:
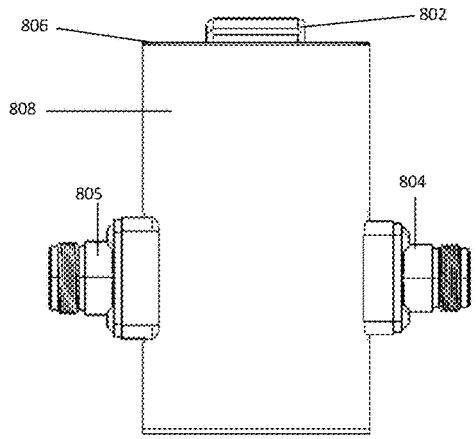
FIG. 8C is a side view of the fourth RF applicator and acoustic receiver sleeve configuration, according to an embodiment.
Figure 8D:
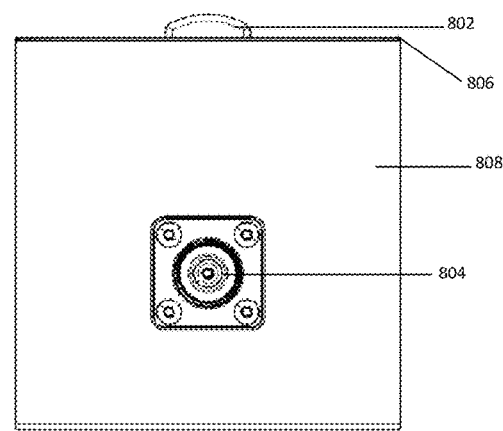
FIG. 8D is a top view of the fourth applicator and acoustic receiver sleeve configuration, according to an embodiment.

In another configuration, an acoustic receiver may have a rectangular shape and be positioned in an elliptical-shaped RF applicator, as shown in FIGS. 8A to 8D. FIG. 8A is a front view of a fourth RF applicator and acoustic receiver sleeve configuration embodiment. FIG. 8B is a perspective view of a fourth RF applicator and acoustic receiver sleeve configuration embodiment. Shown are open-ended hollow elliptical waveguide matching layer 806, open-ended hollow elliptical waveguide body 808, first RF energy feed 804, second RF energy feed 805 rotated 180 degrees about the RF applicator from the first RF energy feed 804, insulation 810, and rectangular acoustic receiver 802 (with rectangular cross-section). FIG. 8C is a side view of a fourth RF applicator and acoustic receiver sleeve configuration embodiment. FIG. 8D is a top view of a fourth applicator and acoustic receiver sleeve configuration embodiment.

Figure 9A:
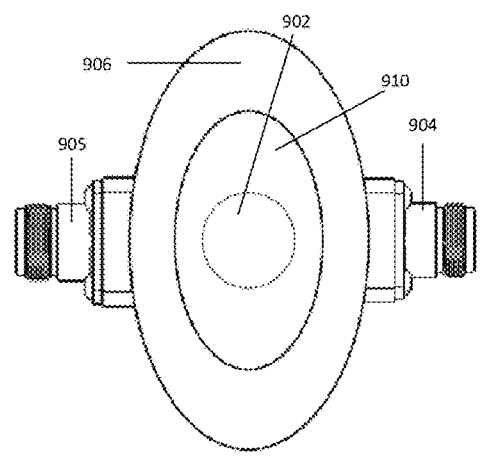
FIG. 9A is a front view of a fifth RF applicator and acoustic receiver sleeve configuration, according to an embodiment.
Figure 9B:
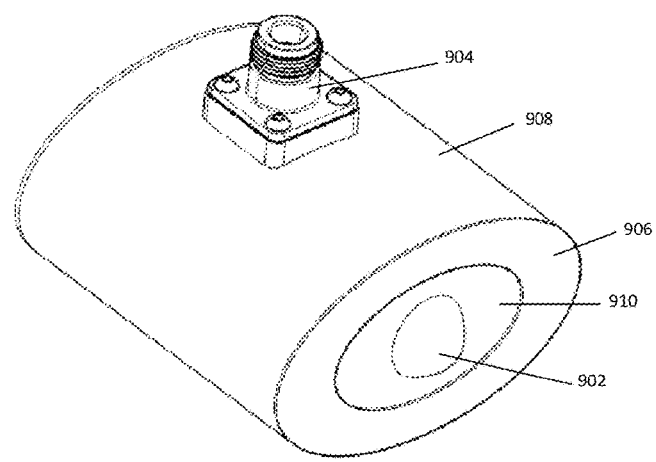
FIG. 9B is a perspective view of the fifth RF applicator and acoustic receiver sleeve configuration, according to an embodiment.
Figure 9C:
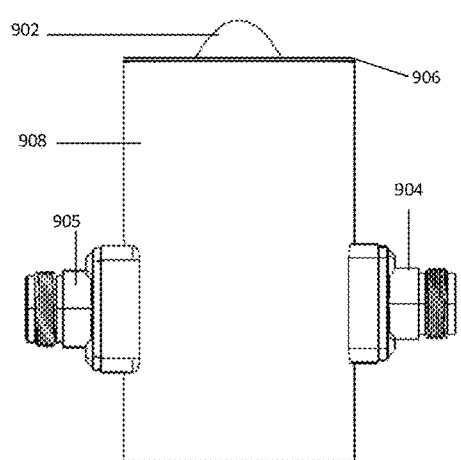
FIG. 9C is a side view of the fifth RF applicator and acoustic receiver sleeve configuration, according to an embodiment.
Figure 9D:
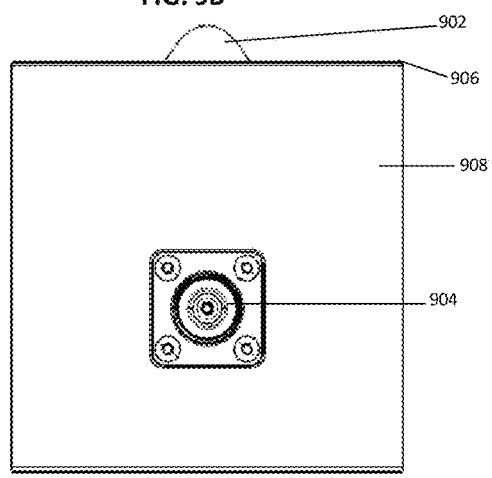
FIG. 9D is a top view of the fifth applicator and acoustic receiver sleeve configuration, according to an embodiment.

In another configuration, an acoustic receiver may have a conical shape and be positioned in an elliptical-shaped RF applicator, as shown in FIGS. 9A to 9D. FIG. 9A is a front view of a fifth RF applicator and acoustic receiver sleeve configuration embodiment. FIG. 9B is a perspective view of a fifth RF applicator and acoustic receiver sleeve configuration embodiment. Shown are open-ended hollow elliptical waveguide matching layer 906, open-ended hollow elliptical waveguide body 908, first RF energy feed 904, second RF energy feed 905 rotated 180 degrees about the RF applicator from the first RF energy feed 904, insulation 910, and conical acoustic receiver 902 (with circular cross-section). FIG. 9C is a side view of a fifth RF applicator and acoustic receiver sleeve configuration embodiment. FIG. 9D is a top view of a fifth applicator and acoustic receiver sleeve configuration embodiment.

FIGS. 10A to 11D show a configuration having a circular acoustic receiver and a rectangular waveguide, as shown in FIGS. 6A to 6D. FIG. 10A is a perspective exploded view of a sixth RF applicator and acoustic receiver sleeve configuration, according to an embodiment. FIG. 10B is a side exploded view of the sixth RF applicator and acoustic receiver sleeve configuration, according to an embodiment. FIG. 10C is a top exploded view of the sixth RF applicator and acoustic receiver sleeve configuration, according to an embodiment. FIG. 10D is a side exploded view of the sixth RF applicator and acoustic receiver sleeve configuration, according to an embodiment.

A waveguide housing 1008 holds a ceramic 1016. A waveguide matching layer 1006 abuts the ceramic 1016 at a first end of the waveguide housing 1008. Acoustic isolation 1010 is positioned inside the waveguide housing 1008. An inner Faraday cage 1012 is positioned inside acoustic isolation 1010. The acoustic isolation 1010 may comprise cork, foam, or the like, and it may be affixed to the ceramic 1016.

In some configurations (not shown), an air gap may be used. The inner Faraday cage 1012 is aligned with a thermoacoustic sensor 1002 having a seal 1014. Although the sensor 1002 is shown as having a rectangular shape and a seal 1014 configured for a rectangular-shaped sensor 1002, it is intended that this configuration may be adapted for other shapes of sensors. The waveguide housing 1008 is coupled to a first RF energy feed 1004 and second RF energy feed 1005 A shielded connector 1018 for the inner Faraday cage 1012 is positioned at a second end of the waveguide housing 1008.

FIGS. 11A to 11D show the components of FIGS. 10A to 10D from an alternative view. FIG. 11A is an alternative perspective exploded view of the sixth RF applicator and acoustic receiver sleeve configuration, according to an embodiment. FIG. 11B is an alternative side exploded view of the sixth RF applicator and acoustic receiver sleeve configuration, according to an embodiment. FIG. 11C is an alternative top exploded view of the sixth RF applicator and acoustic receiver sleeve configuration, according to an embodiment. FIG. 11D is an alternative side exploded view of the sixth RF applicator and acoustic receiver sleeve configuration, according to an embodiment.

FIGS. 12A to 13D show a configuration having a circular acoustic receiver and a rectangular waveguide, as shown in FIGS. 6A to 6D. FIG. 12A is a perspective exploded view of a seventh RF applicator and acoustic receiver sleeve configuration, according to an embodiment. FIG. 12B is a side exploded view of the seventh RF applicator and acoustic receiver sleeve configuration, according to an embodiment. FIG. 12C is a top exploded view of the seventh RF applicator and acoustic receiver sleeve configuration, according to an embodiment. FIG. 12D is a side exploded view of the seventh RF applicator and acoustic receiver sleeve configuration, according to an embodiment.

A waveguide housing 1208 holds a ceramic 1216. Acoustic isolation 1210 is positioned inside the waveguide housing 1008. At an end of the acoustic isolation 1210 is a thermoacoustic sensor (without a lens) 1202. Although the sensor 1202 is shown as having a rectangular shape, it is intended that this configuration may be adapted for other shapes of sensors. Positioned on the sensor 1202 is a front, non-conductive seal 1214, a thin conductive layer 1220, an electromagnetic matching layer 1222, and an acoustic lens 1224. The waveguide housing 1208 is coupled to a first RF energy feed 1204 and second RF energy feed 1205. A shielded connector 1218 and a back conductive seal 1226 are positioned at a second end of the waveguide housing 1208.

FIGS. 13A to 13D show the components of FIGS. 12A to 12D from an alternative view. FIG. 13A is an alternative perspective exploded view of the seventh RF applicator and acoustic receiver sleeve configuration, according to an embodiment. FIG. 13B is an alternative side exploded view of the seventh RF applicator and acoustic receiver sleeve configuration, according to an embodiment. FIG. 13C is an alternative top exploded view of the seventh RF applicator and acoustic receiver sleeve configuration, according to an embodiment. FIG. 13D is an alternative side exploded view of the seventh RF applicator and acoustic receiver sleeve configuration, according to an embodiment.

Figure 14:
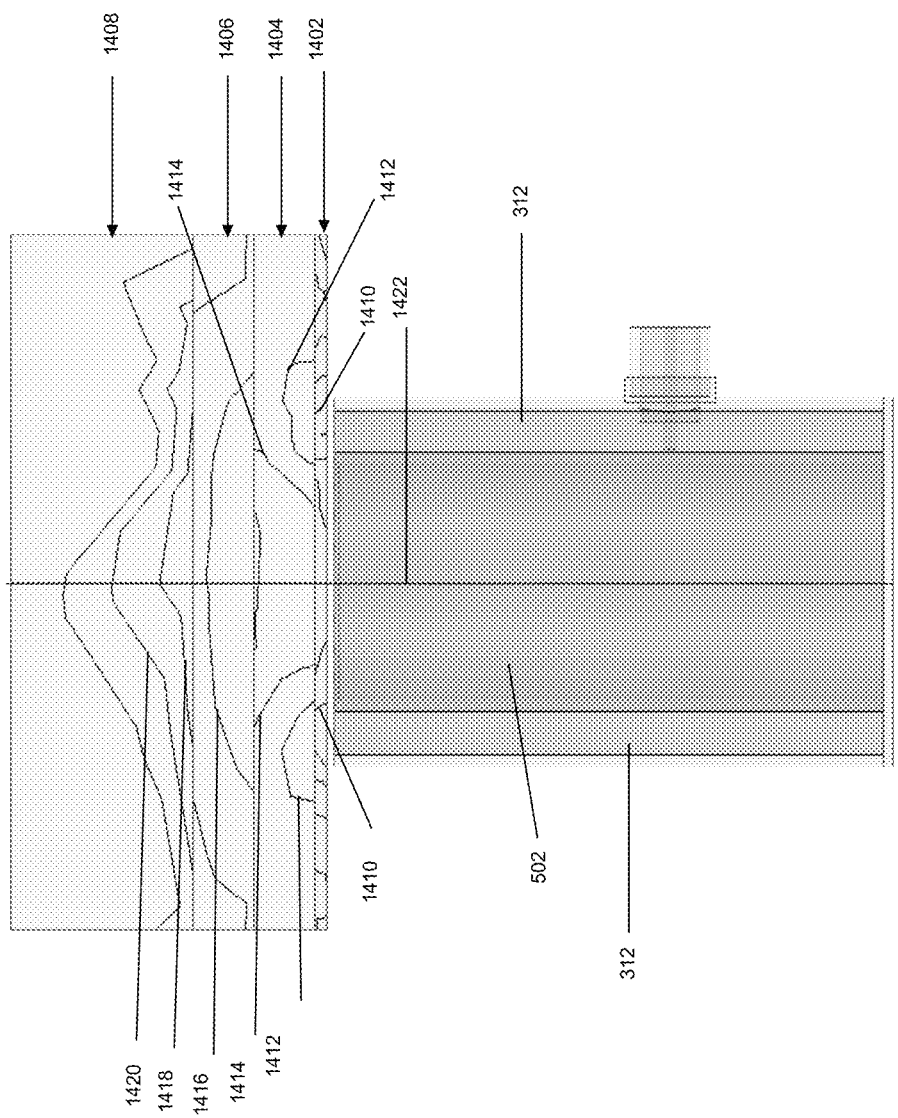
FIG. 14 is a contour map showing electric field strength in decibels in different tissue types for the RF applicator, according to an embodiment.

FIG. 14 is a contour map showing electric field strength in decibels in different tissue types for the open-ended hollow RF applicator 312. The electric field is shown exiting the open-ended hollow RF applicator 312 and traveling through a skin layer 1402, fat layer 1404, muscle layer 1406, and liver layer 1408. Contour line 1410 is 61 decibels, contour line 1412 is 53 decibels, contour line 1414 is 46 decibels, contour line 1416 is 23 decibels, contour line 1418 is 15 decibels, and contour line 1420 is 7 decibels. Peak electric field is shown near the open-ended hollow RF applicator 312 exit. As the electric field is dispersed through the tissue, the electric field becomes strongest near the thermoacoustic probe center axis 1422. Both contour line 1418 and contour line 1420 are located in the liver layer 1408 and are strongest near the thermoacoustic probe center axis 1422. This RF applicator configuration may be preferable to a side-by-side configuration of a RF applicator and acoustic receiver by having a field that converges along the center line and at the deeper end of the tissue rather than the skin layer 1402.

Figure 15:
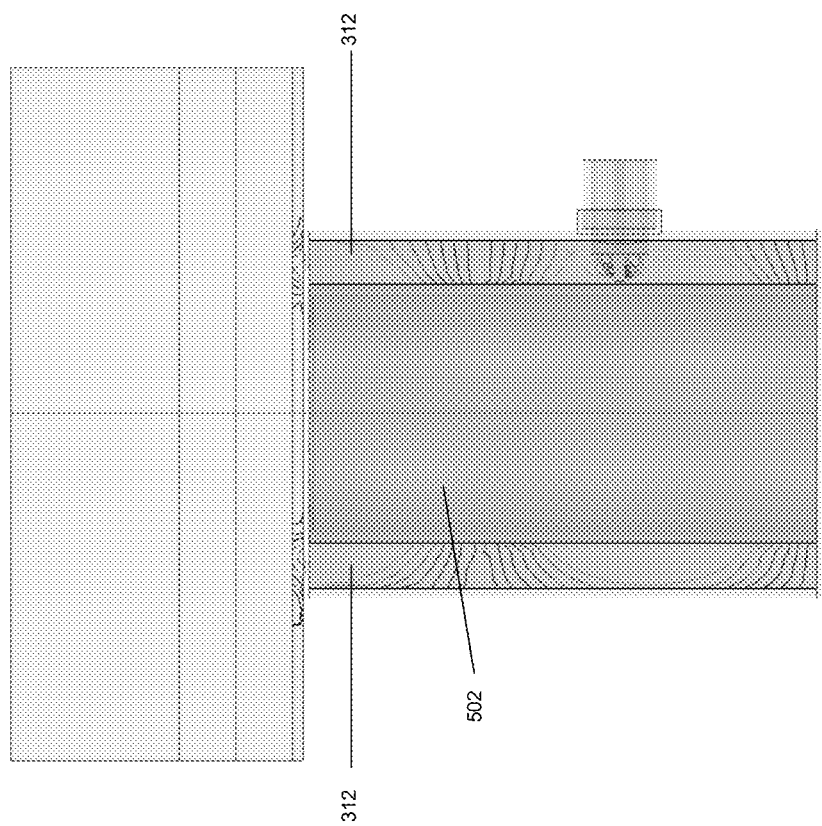
FIG. 15 shows electric field in the RF applicator in volts per meter, according to an embodiment.

FIG. 15 shows electric field in the RF applicator in volts per meter. The hollow cavity 502 has a very low electric field of less than 400 volts per meter. In contrast, the open-ended hollow RF applicator 312 has an electric field that is greater than 1600 volts per meter. The electric field that is generated in the open-ended hollow RF applicator 312 cancels itself in the hollow cavity 502 due to the symmetrical nature (sleeve shape) of the open-ended hollow RF applicator 312 surrounding the hollow cavity 502.

Figure 16:
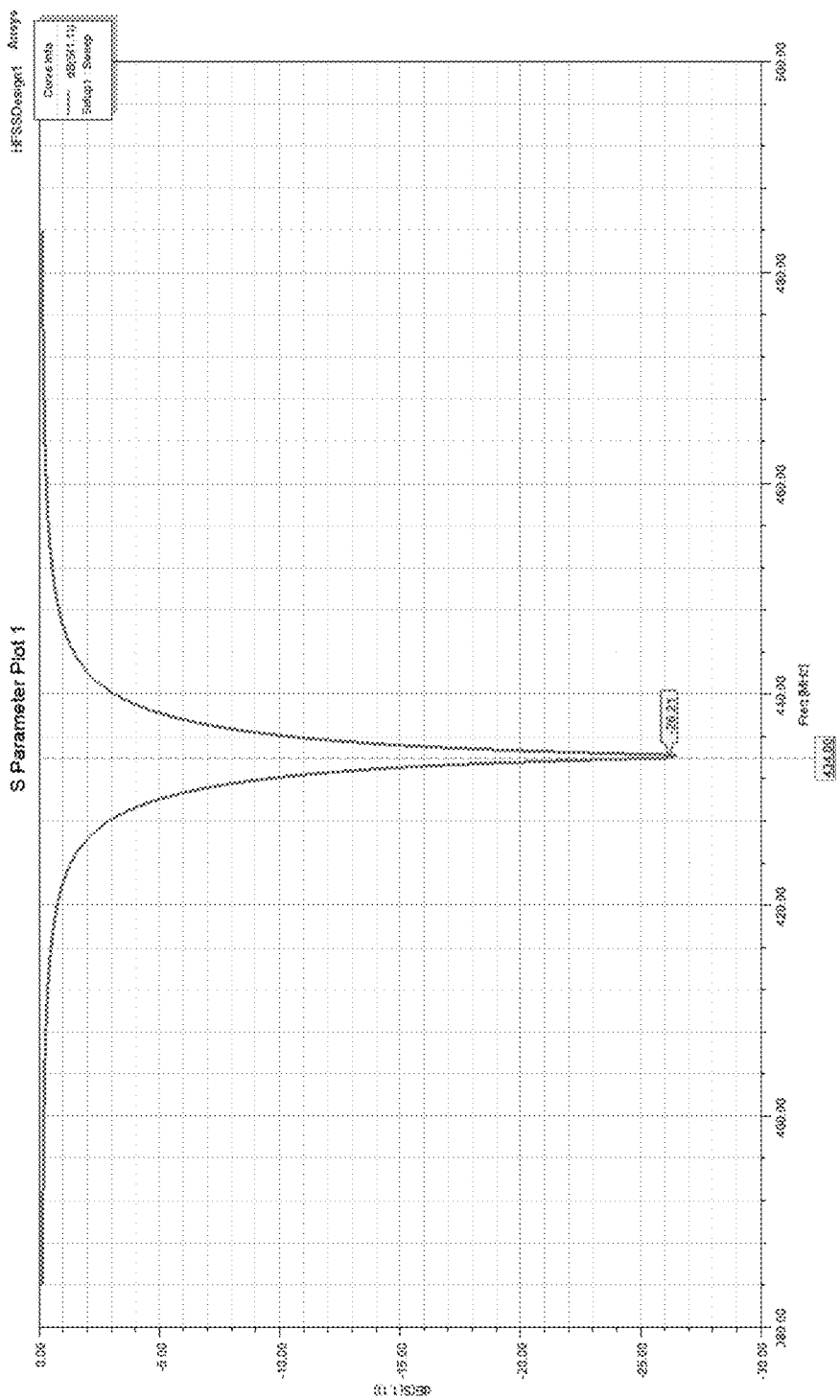
FIG. 16 shows reflected power in decibels at a target frequency for the RF applicator, according to an embodiment.

FIG. 16 shows reflected power in decibels at a target frequency for the open-ended hollow RF applicator 312. FIG. 16 shows the reflection coefficient at a 50 ohm reference impedance versus frequency for the open-ended hollow RF applicator 312. The reflection coefficient represents the amount of power that is transferred from a 50 ohm source into the open-ended hollow RF applicator 312 (i.e., reflected power). At 434 MHz, the design frequency of the open-ended hollow RF applicator 312, the reflection coefficient is −26 dB, which corresponds to 99.75% of the power from a 50 ohm source being transferred to the open-ended hollow RF applicator 312.

By controlling the relative phase and power between individual RF feeds positioned within the RF waveguide housing, the thermoacoustic measurement probe can generate any polarization state of the electromagnetic field: a linear polarization in any direction, a circular or an elliptic polarization.

The thermoacoustic signal response can depend on the polarization of the RF energy that is incident in the tissue of interest. For example, structures, such as blood vessels, may generate a stronger thermoacoustic response if the polarization is parallel to the vessel. Thus, a highly organized tissue will have different electromagnetic properties in different directions. The degree of organization can be assessed by performing multiple measurements with different linear polarizations. In other cases, where the only property of interest is the bulk tissue absorption, a circular polarization may be advantageous as the results are independent of how the operator positions the thermoacoustic measurement probe.

Using multiple feed configurations for the RF applicator, the electric field can be varied at an organ (e.g., liver) or depth of tissue. Some structures, like blood vessels, may be more or less sensitive based on the electric field. The configurations allow for imaging a tumor having a random blood vessel orientation that may be insensitive to a direction of the electric field. The configurations may also be useful to directionally avoid structure, e.g., avoid ribs so that a liver can absorb more energy and provide a better signal back.

FIGS. 17 to 61 represent a an electric field through a layer or layers, such as liver layer 1408. FIGS. 17 to 61 show two feeds of an open-ended hollow RF applicator, where the two feeds may vary in position, amount of power, and may be in a same or different phase from each other. Although only two feeds are shown in these illustrative embodiments, it is intended that two or more feeds may be utilized. The feeds are also shown as being rotated along a circular-shaped RF applicator by 90 degrees, 120 degrees, and 180 degrees, but it is intended that the feeds may be positioned at any angles along the RF applicator. The feeds are also not limited to being positioned at the same depth of the RF applicator.

FIGS. 17 to 28 show a side-view of electric field polarization with two feeds at 90 degrees relative to each other. The side-view of electric field polarization is shown at the face of the open-ended hollow RF applicator 1703. The figures show directional electric field flow vectors at a variety of different phase and power levels for each feed. Smaller arrows 1701 have lower electric field magnitude while larger arrows 1702 have higher electric field magnitude.

Figure 17:
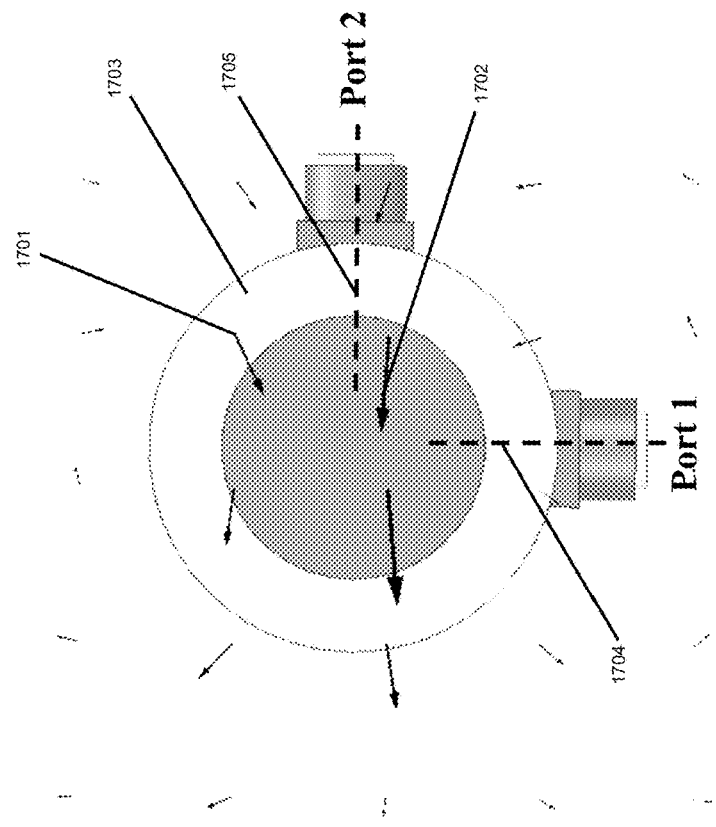
FIG. 17 shows a side-view of electric field polarization with two feeds at 90 degrees relative to each other, according to an embodiment.

FIG. 17 shows a side-view of electric field polarization with two feeds at 90 degrees relative to each other. Feed 1 is at 0 degrees phase and 0 percent power. Feed 2 is at 0 degrees phase and 100 percent power. Port 1 center axis 1704 runs along the center of port 1 and port 2 center axis 1705 runs along the center of port 2. Center axes 1704 and 1705 are shown as non-parallel.

Figure 18:
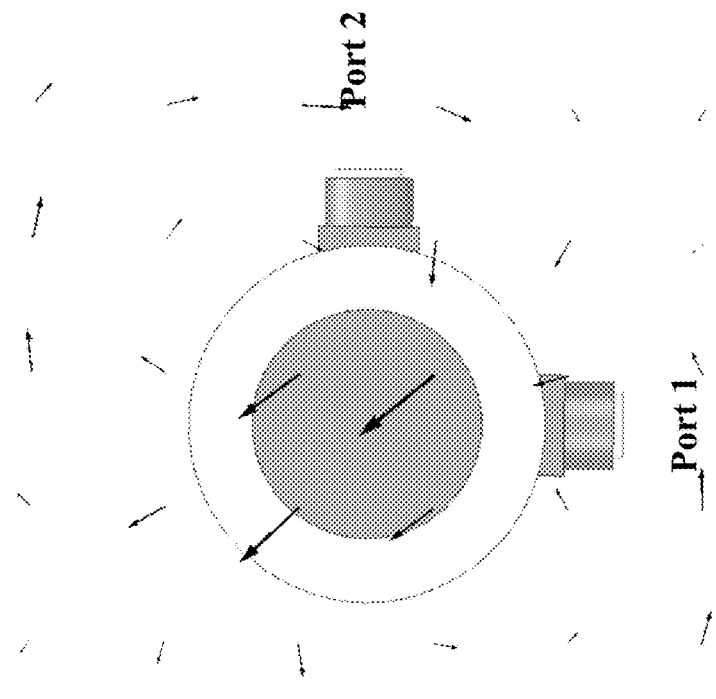
FIG. 18 shows a side-view of electric field polarization with two feeds at 90 degrees relative to each other, according to an embodiment.

FIG. 18 shows a side-view of electric field polarization with two feeds at 90 degrees relative to each other. Feed 1 is at 0 degrees phase and 50 percent power. Feed 2 is at 0 degrees phase and 50 percent power.

FIG. 19 shows a side-view of electric field polarization with two feeds at 90 degrees relative to each other. Feed 1 is at 0 degrees phase and 100 percent power. Feed 2 is at 0 degrees phase and 0 percent power.

FIG. 20 shows a side-view of electric field polarization with two feeds at 90 degrees relative to each other. Feed 1 is at 0 degrees phase and 100 percent power. Feed 2 is at 180 degrees phase and 0 percent power.

Figure 21:
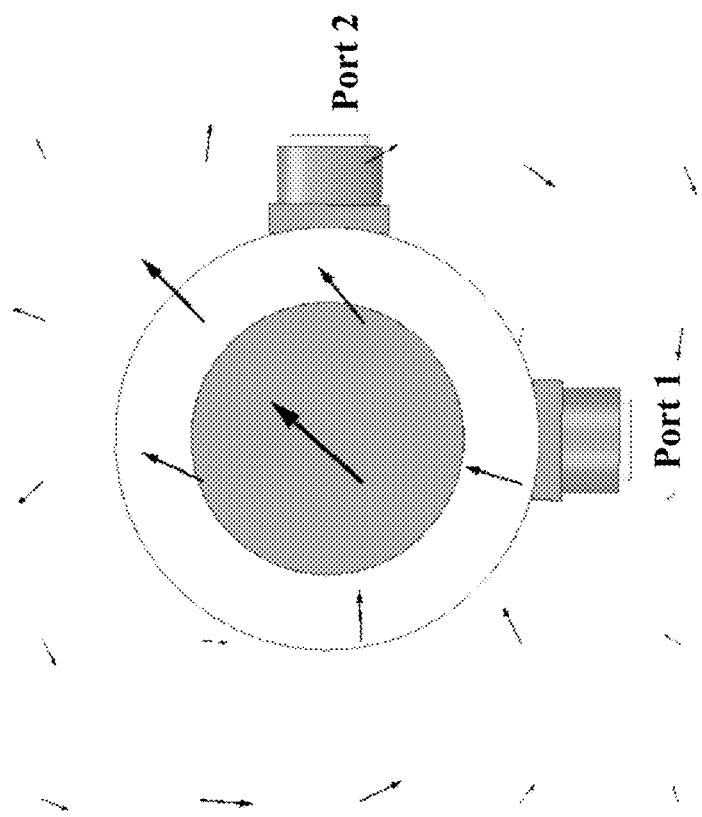
FIG. 21 shows a side-view of electric field polarization with two feeds at 90 degrees relative to each other, according to an embodiment.

FIG. 21 shows a side-view of electric field polarization with two feeds at 90 degrees relative to each other. Feed 1 is at 0 degrees phase and 50 percent power. Feed 2 is at 180 degrees phase and 50 percent power.

Figure 22:
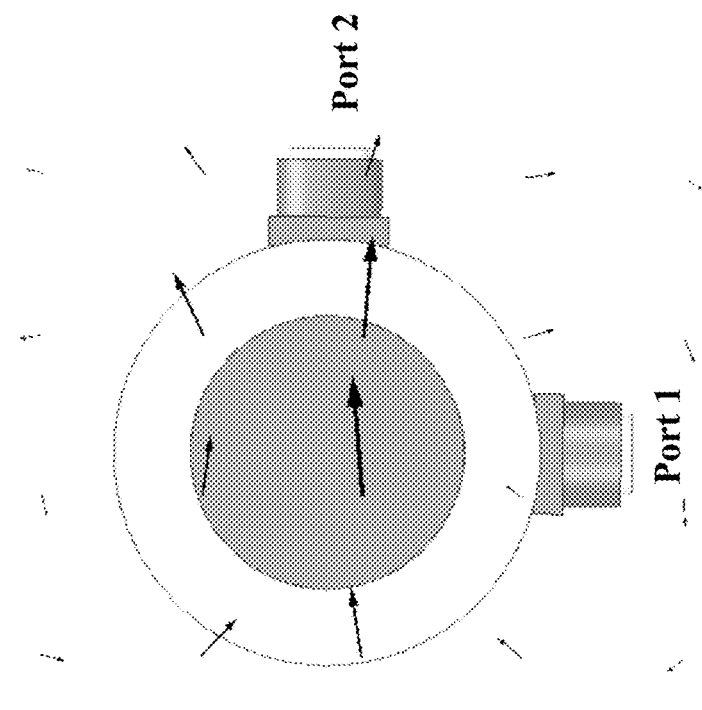
FIG. 22 shows a side-view of electric field polarization with two feeds at 90 degrees relative to each other, according to an embodiment.

FIG. 22 shows a side-view of electric field polarization with two feeds at 90 degrees relative to each other. Feed 1 is at 0 degrees phase and 0 percent power. Feed 2 is at 180 degrees phase and 100 percent power.

Figure 23:
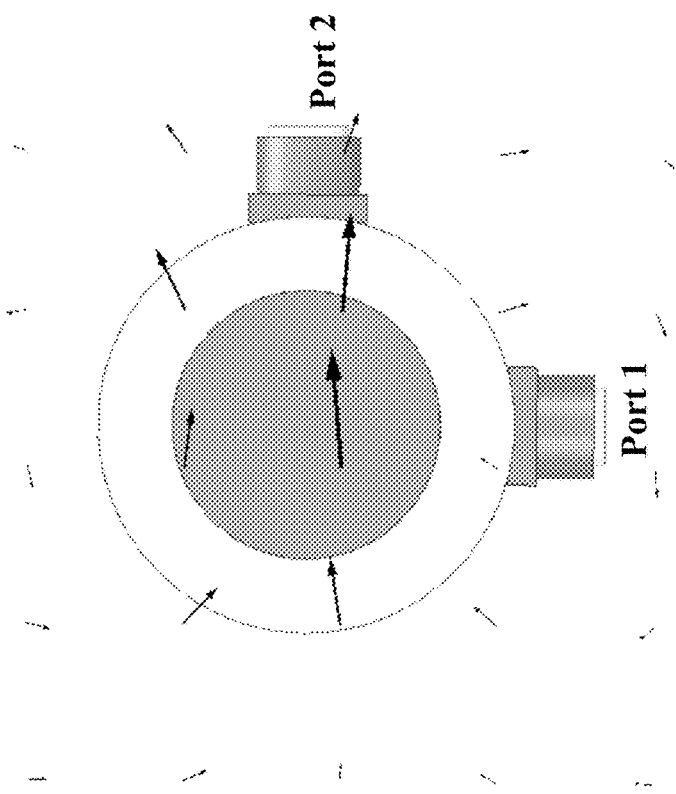
FIG. 23 shows a side-view of electric field polarization with two feeds at 90 degrees relative to each other, according to an embodiment.

FIG. 23 shows a side-view of electric field polarization with two feeds at 90 degrees relative to each other. Feed 1 is at 180 degrees phase and 0 percent power. Feed 2 is at 180 degrees phase and 100 percent power.

Figure 24:
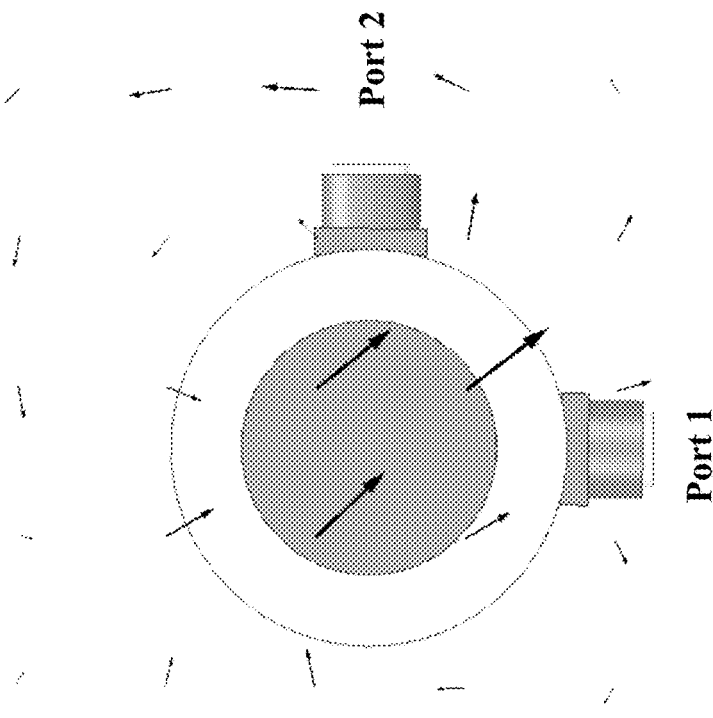
FIG. 24 shows a side-view of electric field polarization with two feeds at 90 degrees relative to each other, according to an embodiment.

FIG. 24 shows a side-view of electric field polarization with two feeds at 90 degrees relative to each other. Feed 1 is at 180 degrees phase and 50 percent power. Feed 2 is at 180 degrees phase and 50 percent power.

Figure 25:
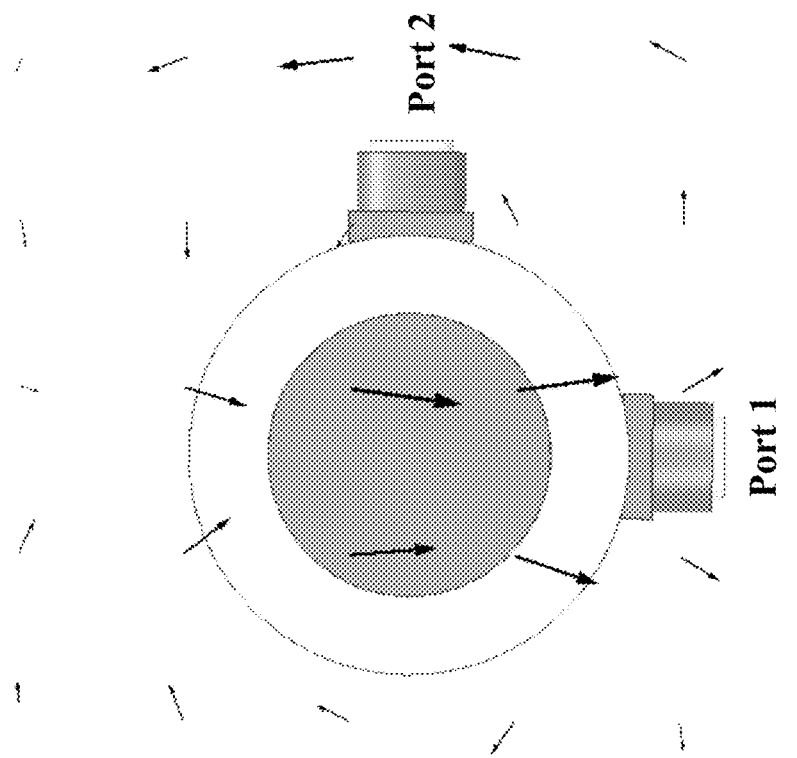
FIG. 25 shows a side-view of electric field polarization with two feeds at 90 degrees relative to each other, according to an embodiment.

FIG. 25 shows a side-view of electric field polarization with two feeds at 90 degrees relative to each other. Feed 1 is at 180 degrees phase and 100 percent power. Feed 2 is at 180 degrees phase and 0 percent power.

Figure 26:
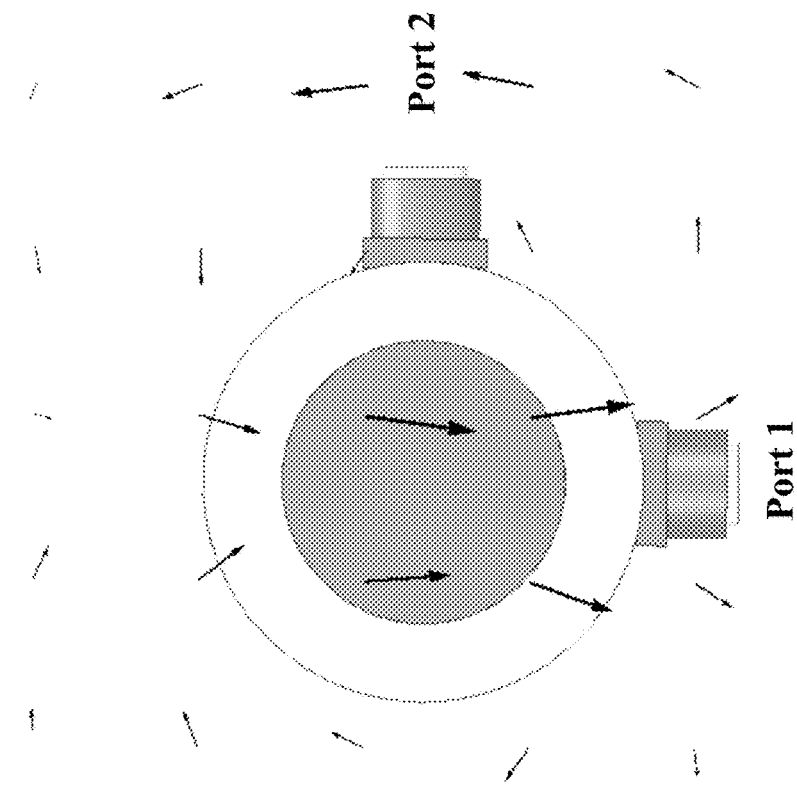
FIG. 26 shows a side-view of electric field polarization with two feeds at 90 degrees relative to each other, according to an embodiment.

FIG. 26 shows a side-view of electric field polarization with two feeds at 90 degrees relative to each other. Feed 1 is at 180 degrees phase and 100 percent power. Feed 2 is at 0 degrees phase and 0 percent power.

Figure 27:
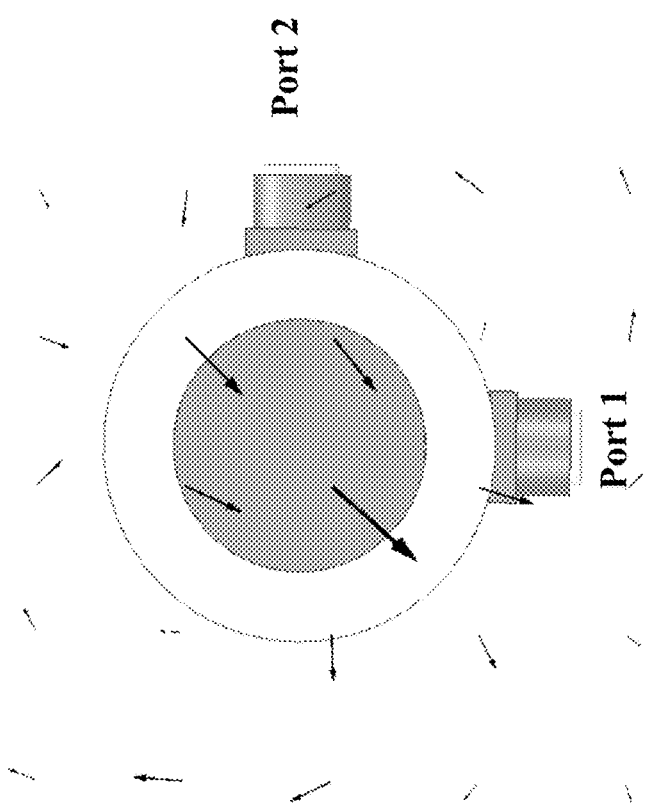
FIG. 27 shows a side-view of electric field polarization with two feeds at 90 degrees relative to each other, according to an embodiment.

FIG. 27 shows a side-view of electric field polarization with two feeds at 90 degrees relative to each other. Feed 1 is at 180 degrees phase and 50 percent power. Feed 2 is at 0 degrees phase and 50 percent power.

Figure 28:
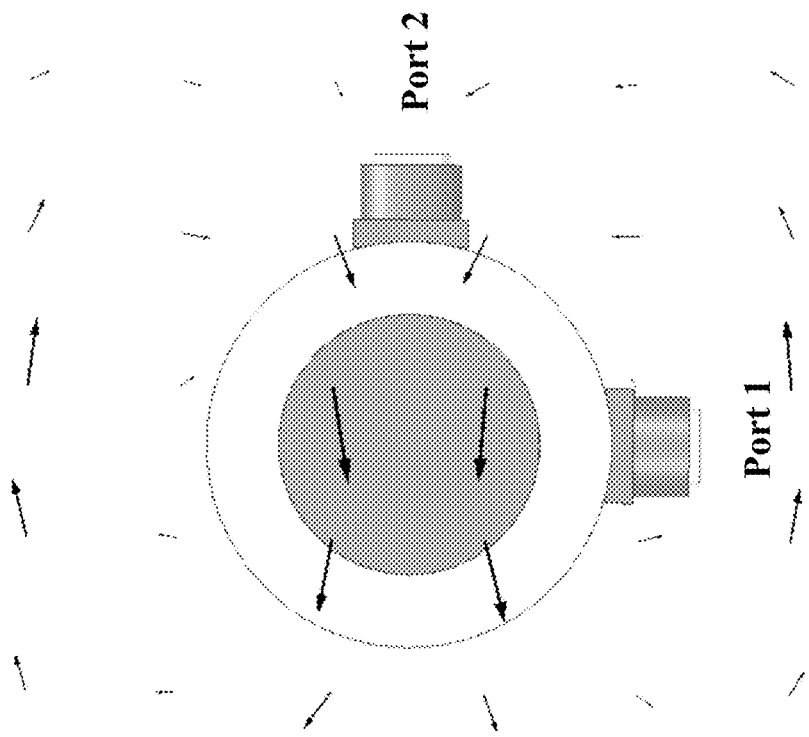
FIG. 28 shows a side-view of electric field polarization with two feeds at 90 degrees relative to each other, according to an embodiment.

FIG. 28 shows a side-view of electric field polarization with two feeds at 90 degrees relative to each other. Feed 1 is at 180 degrees phase and 0 percent power. Feed 2 is at 0 degrees phase and 100 percent power.

FIGS. 29A-29F show a side-view of electric field polarization with two feeds at 90 degrees relative to each other at six different points in a cycle, according to an embodiment. The electric field polarizations are shown at different phases of a cycle: 0 degrees, 72 degrees, 144 degrees, 216 degrees, 288 degrees, and 360 degrees (which is the same as 0 degrees).

Figure 30:
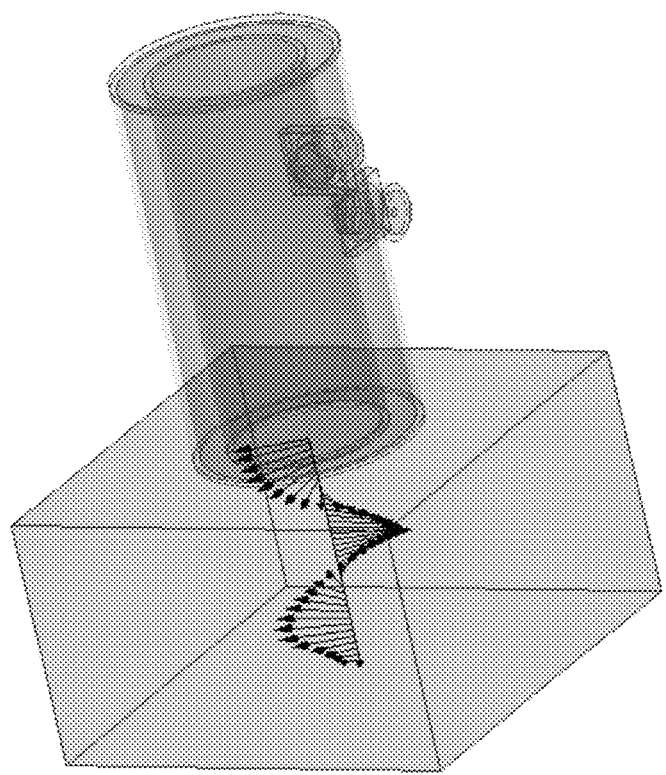
FIG. 30 shows an isometric view of electric field polarization with two feeds at 90 degrees relative to each other at a varying distance into tissue, according to an embodiment.

FIG. 30 shows an isometric view of electric field polarization with two feeds at 90 degrees relative to each other at a varying distance into tissue, according to an embodiment. Feed 1 is at 0 degrees phase and 50 percent power. Feed 2 is at 90 degrees phase and 50 percent power. Directional energy vectors are shown rotating about an axis that is perpendicular to the center of the face of the RF applicator 312. These energy vectors rotate 360 degrees per cycle about the axis that is perpendicular to the center of the face of the RF applicator 312.

Figure 31:
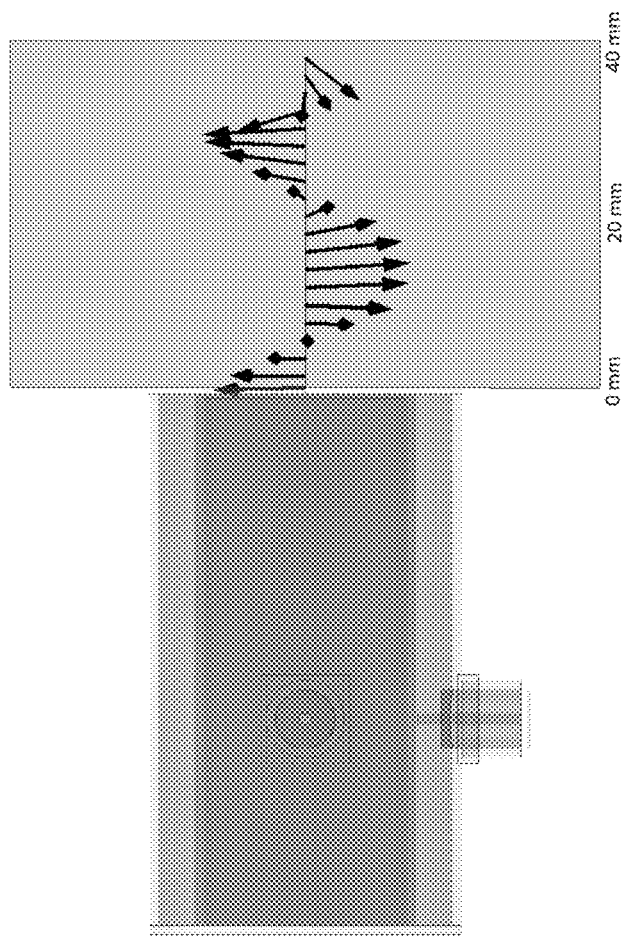
FIG. 31 shows a side-view of electric field polarization with two feeds at 90 degrees relative to each other at a varying distance into tissue, according to an embodiment.

FIG. 31 shows a side-view of electric field polarization with two feeds at 90 degrees relative to each other at a varying distance into tissue. Feed 1 is at 0 degrees phase and 50 percent power. Feed 2 is at 90 degrees phase and 50 percent power. Directional energy vectors are shown rotating about an axis that is perpendicular to the center of the face of the RF applicator 312. These energy vectors rotate 360 degrees per cycle about the axis that is perpendicular to the center of the face of the RF applicator 312.

FIGS. 32 to 43 show a side-view of electric field polarization with two feeds at 180 degrees relative to each other. The side-view of electric field polarization is shown at the face of the open-ended hollow RF applicator 1703. The figures show directional electric field flow vectors at a variety of different phase and power levels for each feed. Smaller arrows 1701 have lower electric field magnitude while larger arrows 1702 have higher electric field magnitude.

Figure 32:
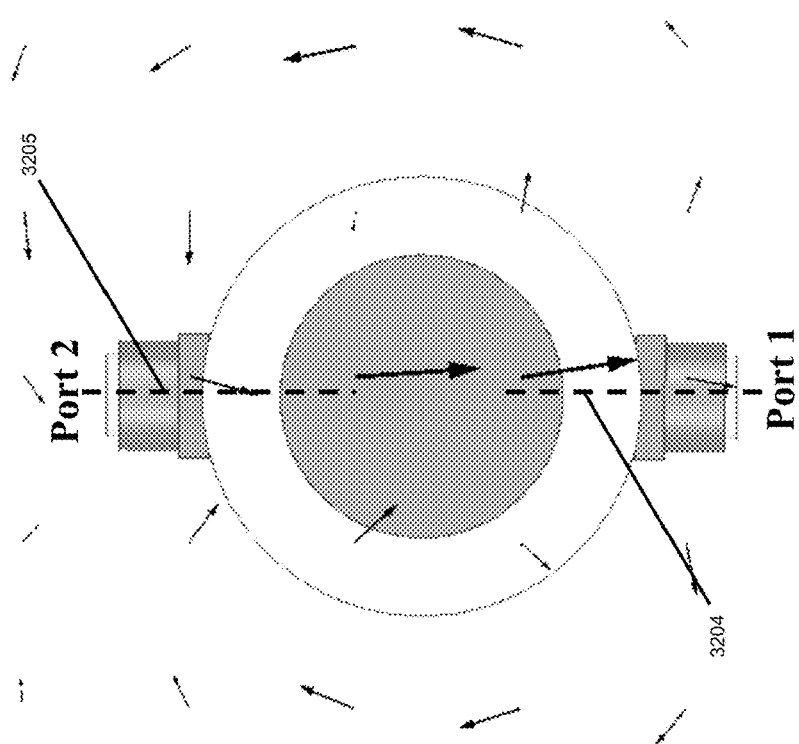
FIG. 32 shows a side-view of electric field polarization with two feeds at 180 degrees relative to each other, according to an embodiment.

FIG. 32 shows a side-view of electric field polarization with two feeds at 180 degrees relative to each other. Feed 1 is at 0 degrees phase and 0 percent power. Feed 2 is at 0 degrees phase and 100 percent power. Port 1 center axis 3204 runs along the center of port 1 and port 2 center axis 3205 runs along the center of port 2. Center axes 3204 and 3205 are shown as parallel.

Figure 33:
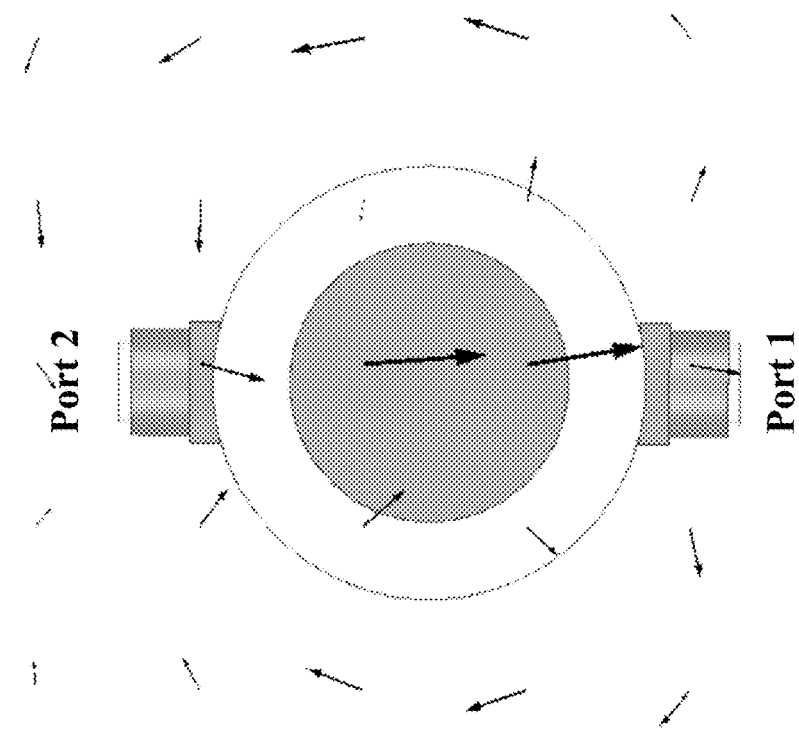
FIG. 33 shows a side-view of electric field polarization with two feeds at 180 degrees relative to each other, according to an embodiment.

FIG. 33 shows a side-view of electric field polarization with two feeds at 180 degrees relative to each other. Feed 1 is at 0 degrees phase and 50 percent power. Feed 2 is at 0 degrees phase and 50 percent power.

Figure 34:
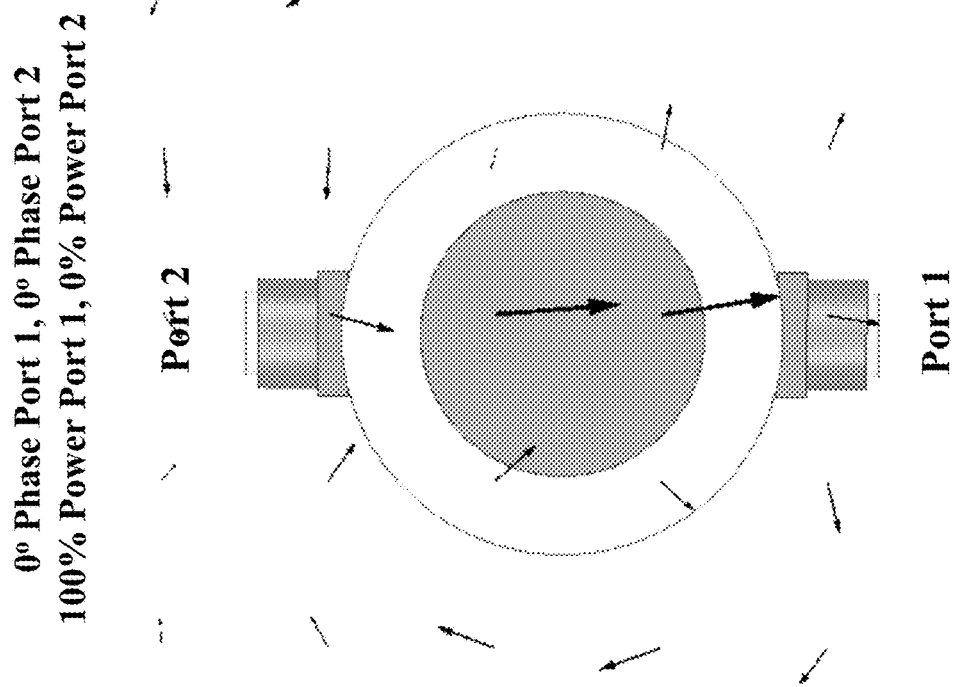
FIG. 34 shows a side-view of electric field polarization with two feeds at 180 degrees relative to each other, according to an embodiment.

FIG. 34 shows a side-view of electric field polarization with two feeds at 180 degrees relative to each other. Feed 1 is at 0 degrees phase and 100 percent power. Feed 2 is at 0 degrees phase and 0 percent power.

Figure 35:
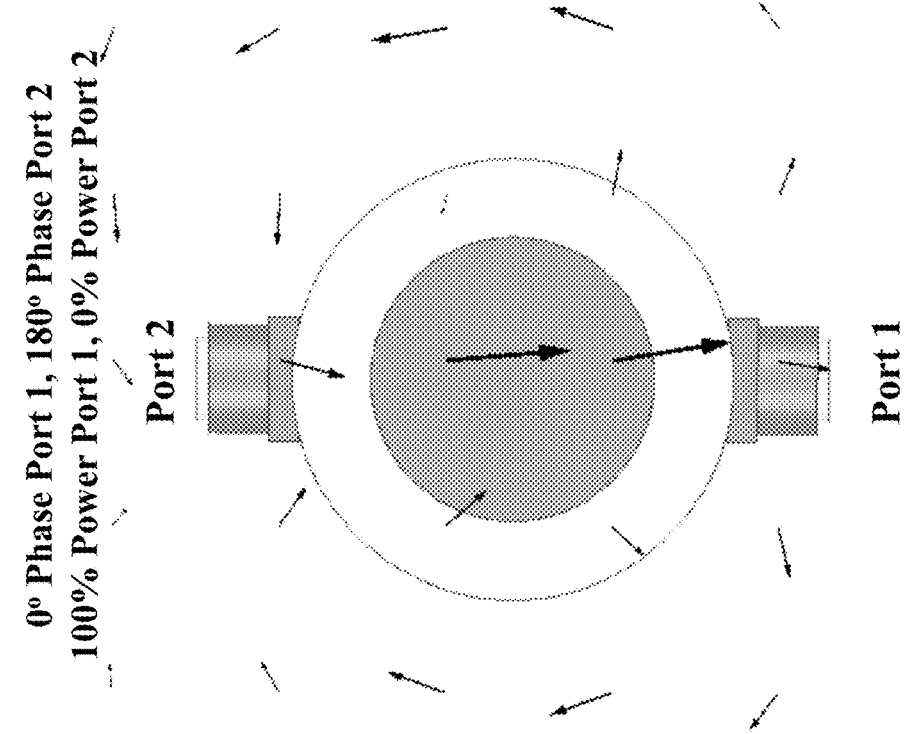
FIG. 35 shows a side-view of electric field polarization with two feeds at 180 degrees relative to each other, according to an embodiment.

FIG. 35 shows a side-view of electric field polarization with two feeds at 180 degrees relative to each other. Feed 1 is at 0 degrees phase and 100 percent power. Feed 2 is at 180 degrees phase and 0 percent power.

Figure 36:
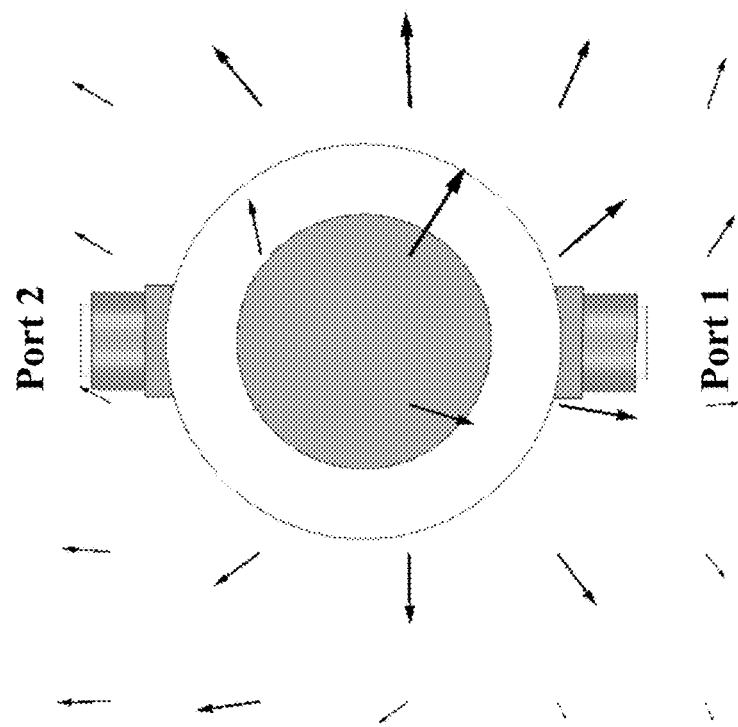
FIG. 36 shows a side-view of electric field polarization with two feeds at 180 degrees relative to each other, according to an embodiment.

FIG. 36 shows a side-view of electric field polarization with two feeds at 180 degrees relative to each other. Feed 1 is at 0 degrees phase and 50 percent power. Feed 2 is at 180 degrees phase and 50 percent power.

Figure 37:
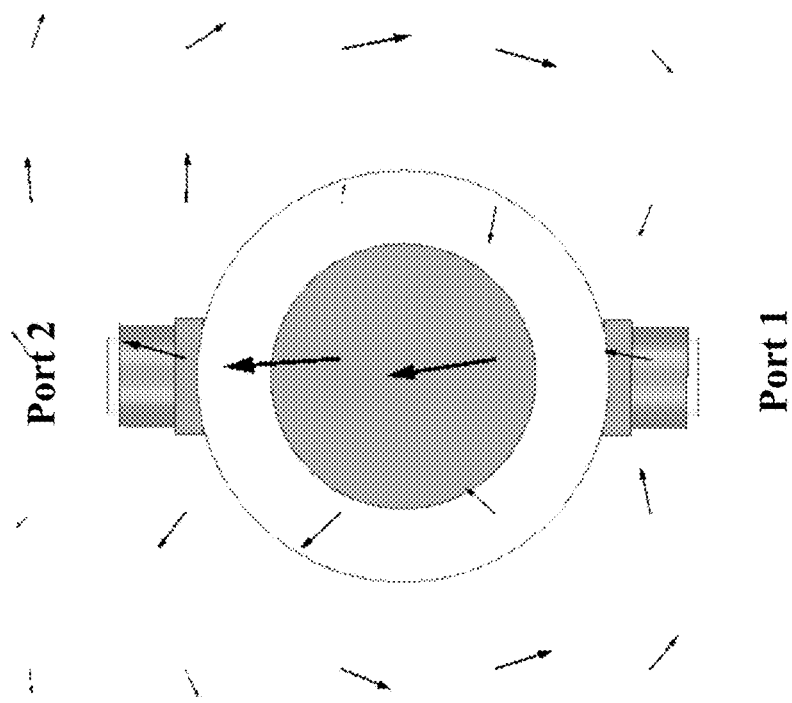
FIG. 37 shows a side-view of electric field polarization with two feeds at 180 degrees relative to each other, according to an embodiment.

FIG. 37 shows a side-view of electric field polarization with two feeds at 180 degrees relative to each other. Feed 1 is at 0 degrees phase and 0 percent power. Feed 2 is at 180 degrees phase and 100 percent power.

Figure 38:
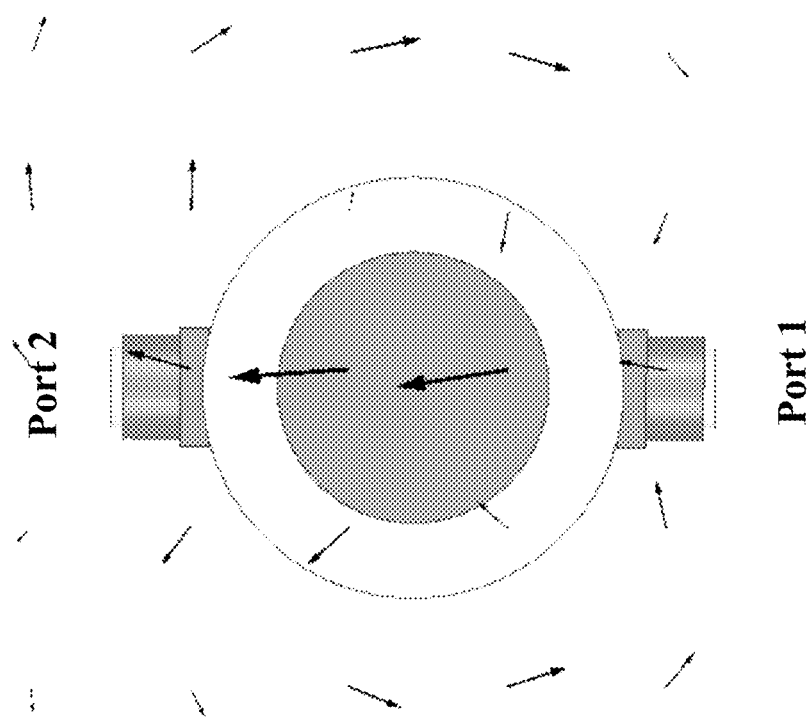
FIG. 38 shows a side-view of electric field polarization with two feeds at 180 degrees relative to each other, according to an embodiment.

FIG. 38 shows a side-view of electric field polarization with two feeds at 180 degrees relative to each other. Feed 1 is at 180 degrees phase and 0 percent power. Feed 2 is at 180 degrees phase and 100 percent power.

Figure 39:
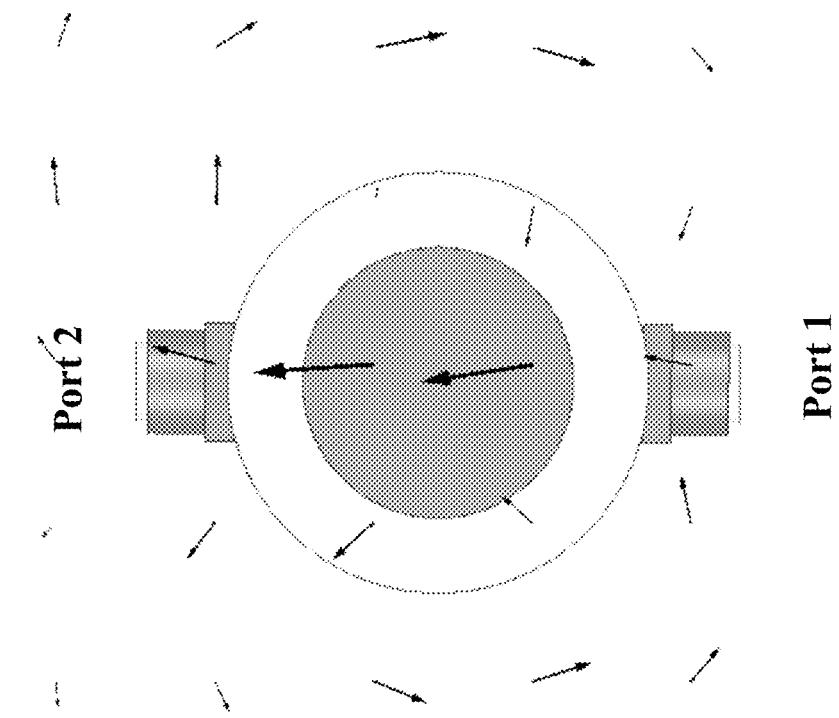
FIG. 39 shows a side-view of electric field polarization with two feeds at 180 degrees relative to each other, according to an embodiment.

FIG. 39 shows a side-view of electric field polarization with two feeds at 180 degrees relative to each other. Feed 1 is at 180 degrees phase and 50 percent power. Feed 2 is at 180 degrees phase and 50 percent power.

Figure 40:
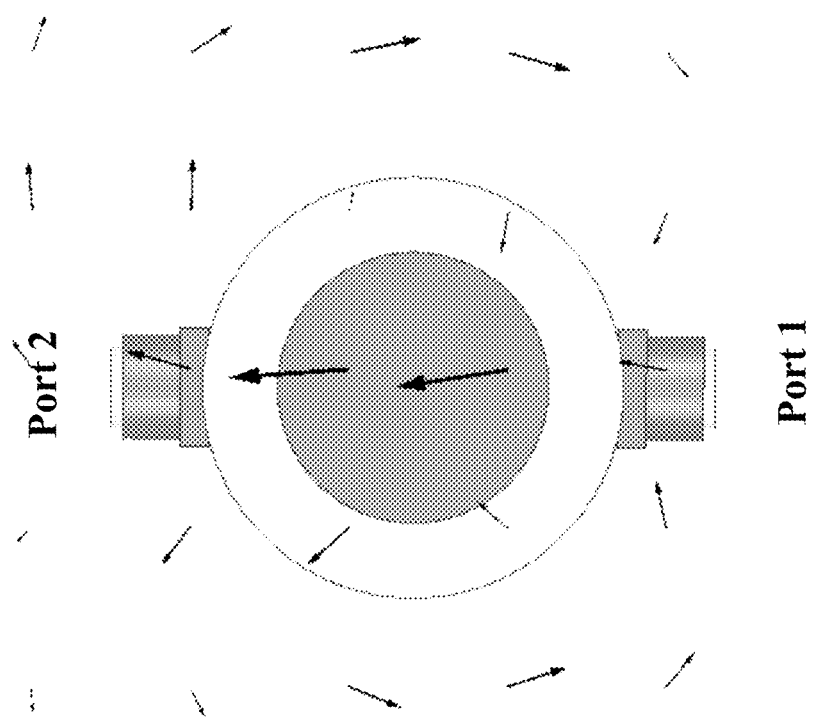
FIG. 40 shows a side-view of electric field polarization with two feeds at 180 degrees relative to each other, according to an embodiment.

FIG. 40 shows a side-view of electric field polarization with two feeds at 180 degrees relative to each other. Feed 1 is at 180 degrees phase and 100 percent power. Feed 2 is at 180 degrees phase and 0 percent power.

Figure 41:
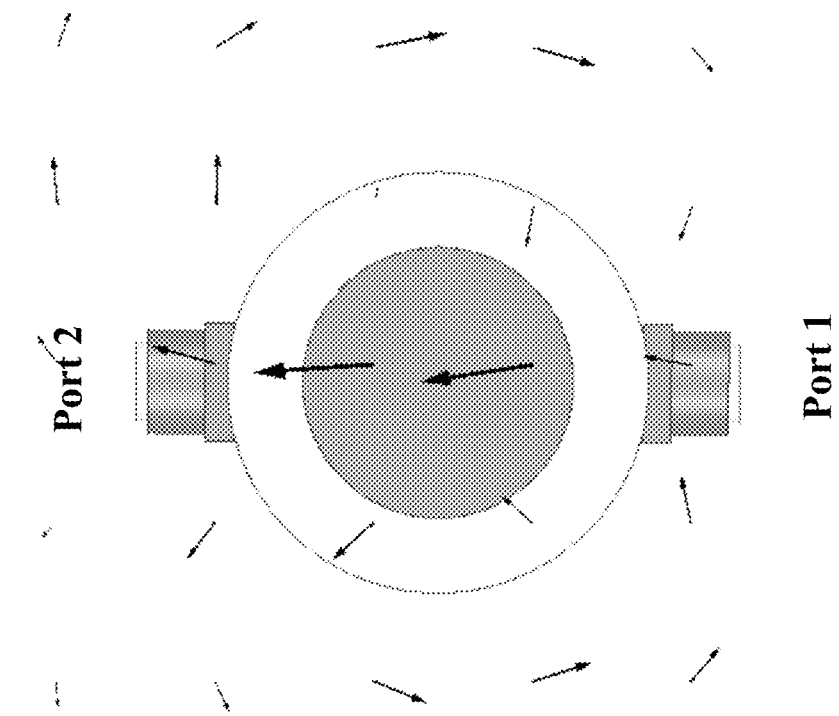
FIG. 41 shows a side-view of electric field polarization with two feeds at 180 degrees relative to each other, according to an embodiment.

FIG. 41 shows a side-view of electric field polarization with two feeds at 180 degrees relative to each other. Feed 1 is at 180 degrees phase and 100 percent power. Feed 2 is at 0 degrees phase and 0 percent power.

Figure 42:
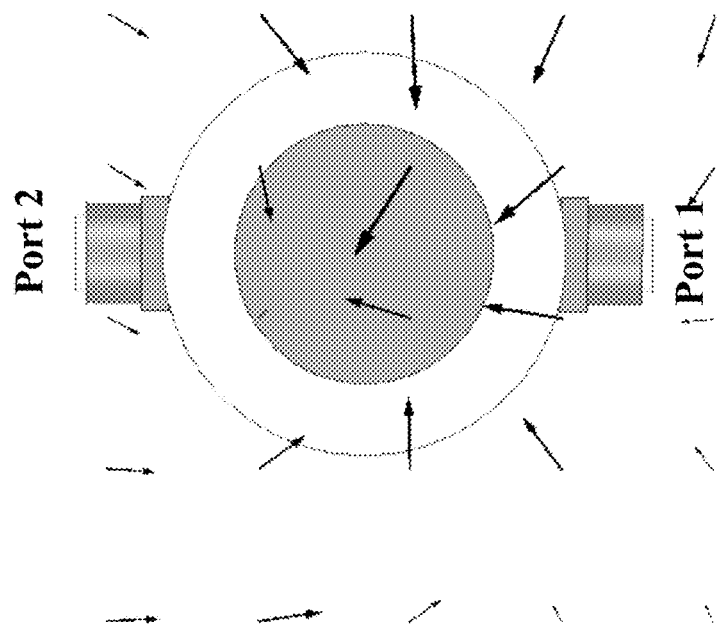
FIG. 42 shows a side-view of electric field polarization with two feeds at 180 degrees relative to each other, according to an embodiment.

FIG. 42 shows a side-view of electric field polarization with two feeds at 180 degrees relative to each other. Feed 1 is at 180 degrees phase and 50 percent power. Feed 2 is at 0 degrees phase and 50 percent power.

Figure 43:
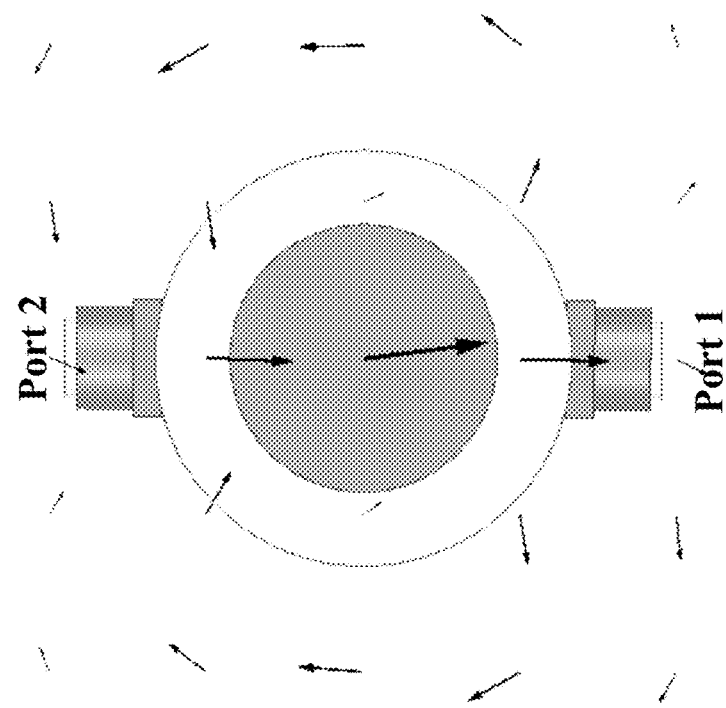
FIG. 43 shows a side-view of electric field polarization with two feeds at 180 degrees relative to each other, according to an embodiment.

FIG. 43 shows a side-view of electric field polarization with two feeds at 180 degrees relative to each other. Feed 1 is at 180 degrees phase and 0 percent power. Feed 2 is at 0 degrees phase and 100 percent power.

FIGS. 44A-44F show a side-view of electric field polarization with two feeds at 180 degrees relative to each other at six different points in a cycle, according to an embodiment. The electric field polarizations are shown at different phases of a cycle: 0 degrees, 72 degrees, 144 degrees, 216 degrees, 288 degrees, and 360 degrees (which is the same as 0 degrees).

Figure 45:
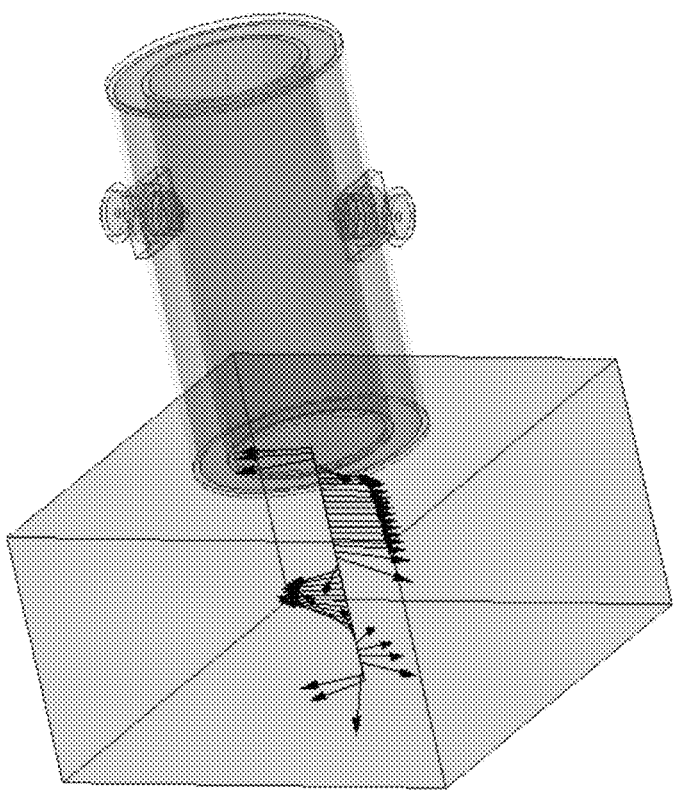
FIG. 45 shows an isometric view of electric field polarization with two feeds at 180 degrees relative to each other at a varying distance into tissue, according to an embodiment.

FIG. 45 shows an isometric view of electric field polarization with two feeds at 180 degrees relative to each other at a varying distance into tissue, according to an embodiment. Feed 1 is at 0 degrees phase and 50 percent power. Feed 2 is at 90 degrees phase and 50 percent power. Directional energy vectors are shown rotating about an axis that is perpendicular to the center of the face of the RF applicator 312. These energy vectors rotate 360 degrees per cycle about the axis that is perpendicular to the center of the face of the RF applicator 312.

Figure 46:
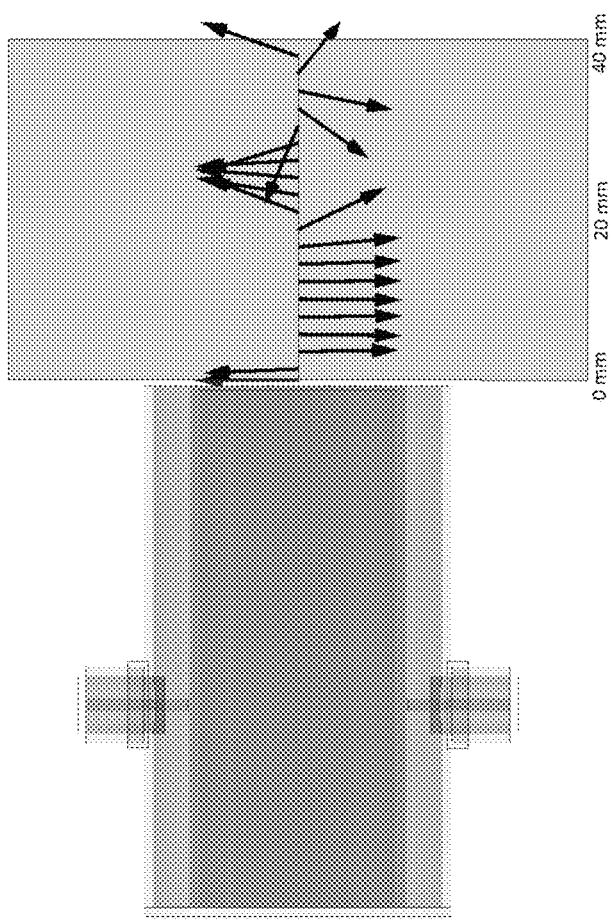
FIG. 46 shows a side-view of electric field polarization with two feeds at 180 degrees relative to each other at a varying distance into tissue, according to an embodiment.

FIG. 46 shows a side-view of electric field polarization with two feeds at 180 degrees relative to each other at a varying distance into tissue. Feed 1 is at 0 degrees phase and 50 percent power. Feed 2 is at 90 degrees phase and 50 percent power. Directional energy vectors are shown rotating about an axis that is perpendicular to the center of the face of the RF applicator 312. These energy vectors rotate 360 degrees per cycle about the axis that is perpendicular to the center of the face of the RF applicator 312.

FIGS. 47 to 58 show a side-view of electric field polarization with two feeds at 120 degrees relative to each other. The side-view of electric field polarization is shown at the face of the open-ended hollow RF applicator 1703. The figures show directional electric field flow vectors at a variety of different phase and power levels for each feed. Smaller arrows 1701 have lower electric field magnitude while larger arrows 1702 have higher electric field magnitude.

Figure 47:
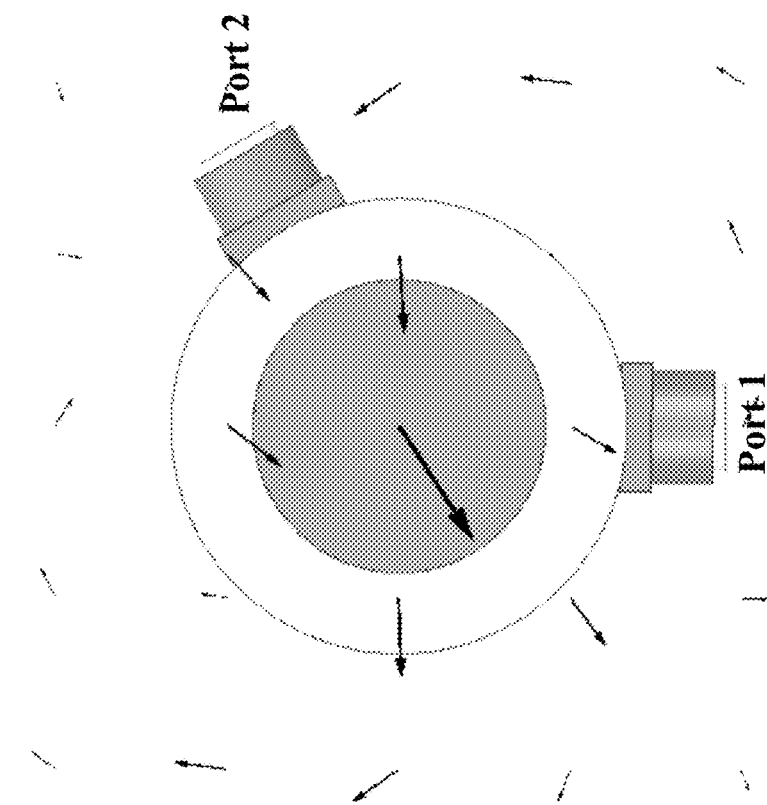
FIG. 47 shows a side-view of electric field polarization with two feeds at 120 degrees relative to each other, according to an embodiment.

FIG. 47 shows a side-view of electric field polarization with two feeds at 120 degrees relative to each other. Feed 1 is at 0 degrees phase and 0 percent power. Feed 2 is at 0 degrees phase and 100 percent power.

Figure 48:
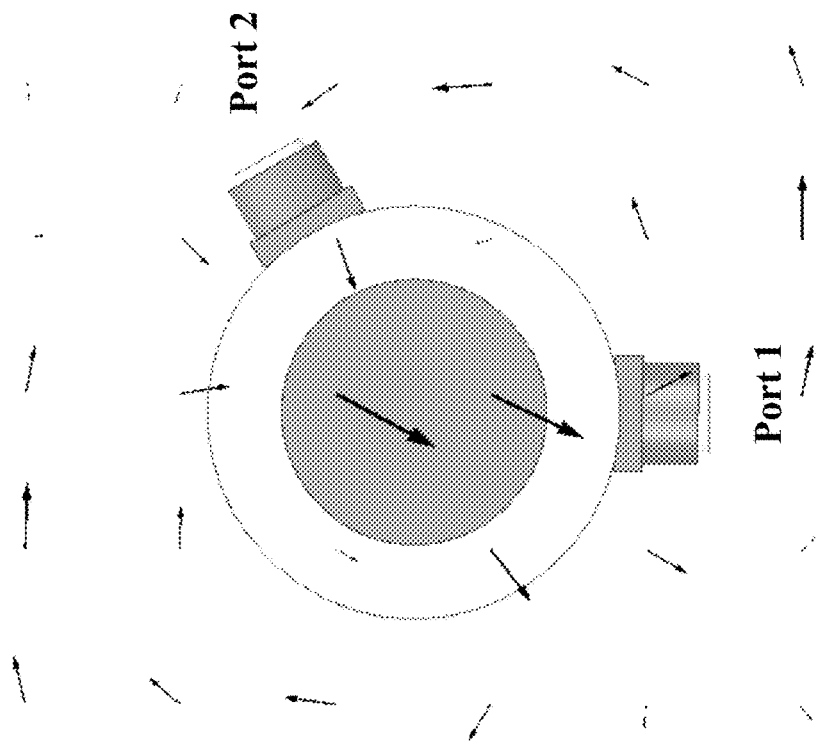
FIG. 48 shows a side-view of electric field polarization with two feeds at 120 degrees relative to each other, according to an embodiment.

FIG. 48 shows a side-view of electric field polarization with two feeds at 120 degrees relative to each other. Feed 1 is at 0 degrees phase and 50 percent power. Feed 2 is at 0 degrees phase and 50 percent power.

Figure 49:
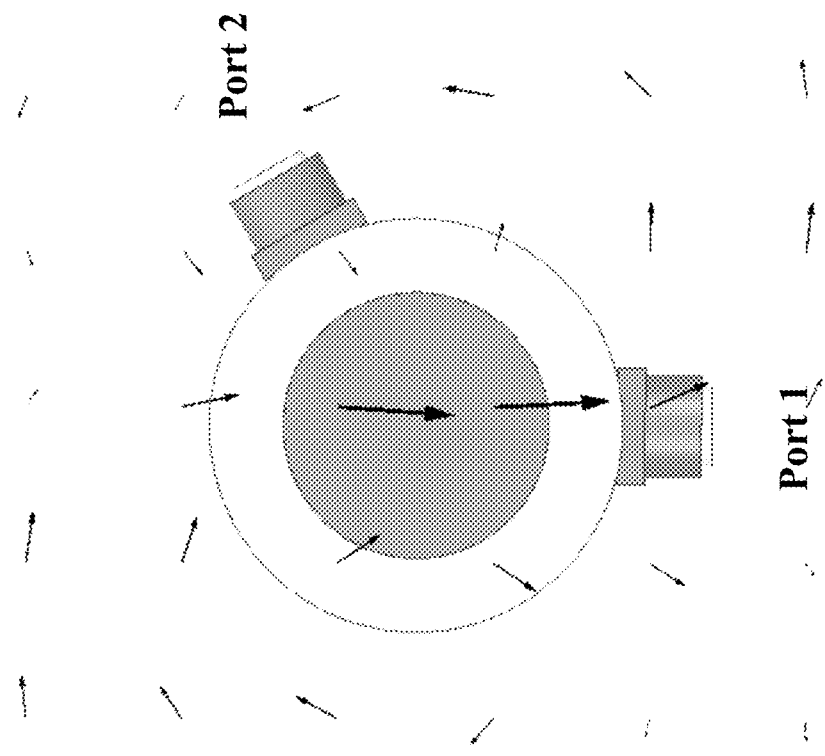
FIG. 49 shows a side-view of electric field polarization with two feeds at 120 degrees relative to each other, according to an embodiment.

FIG. 49 shows a side-view of electric field polarization with two feeds at 120 degrees relative to each other. Feed 1 is at 0 degrees phase and 100 percent power. Feed 2 is at 0 degrees phase and 0 percent power.

Figure 50:
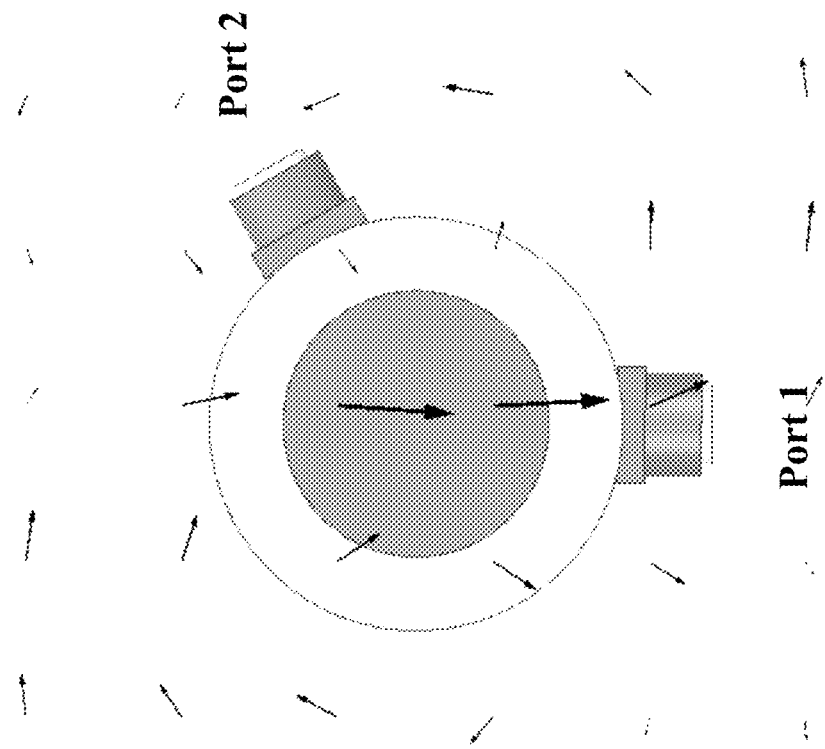
FIG. 50 shows a side-view of electric field polarization with two feeds at 120 degrees relative to each other, according to an embodiment.

FIG. 50 shows a side-view of electric field polarization with two feeds at 120 degrees relative to each other. Feed 1 is at 0 degrees phase and 100 percent power. Feed 2 is at 180 degrees phase and 0 percent power.

Figure 51:
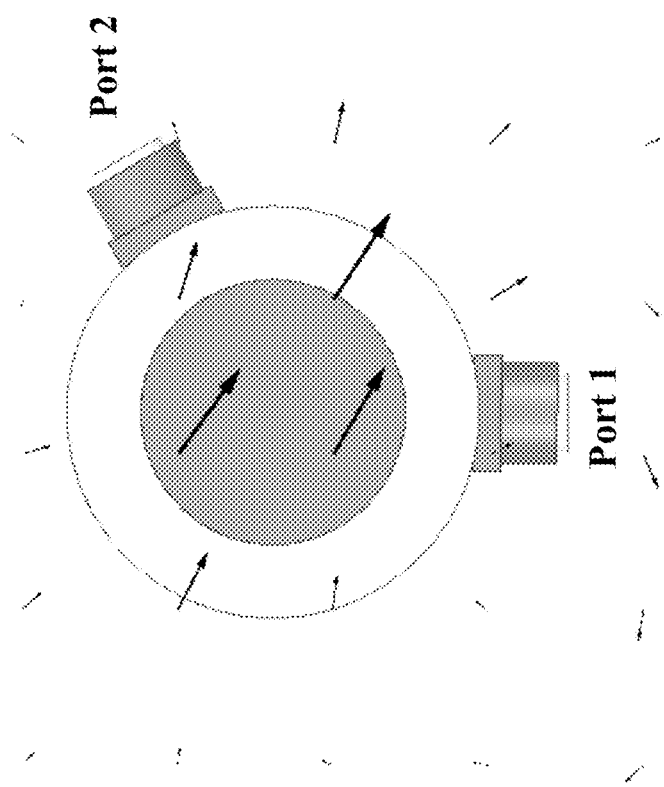
FIG. 51 shows a side-view of electric field polarization with two feeds at 120 degrees relative to each other, according to an embodiment.

FIG. 51 shows a side-view of electric field polarization with two feeds at 120 degrees relative to each other. Feed 1 is at 0 degrees phase and 50 percent power. Feed 2 is at 180 degrees phase and 50 percent power.

Figure 52:
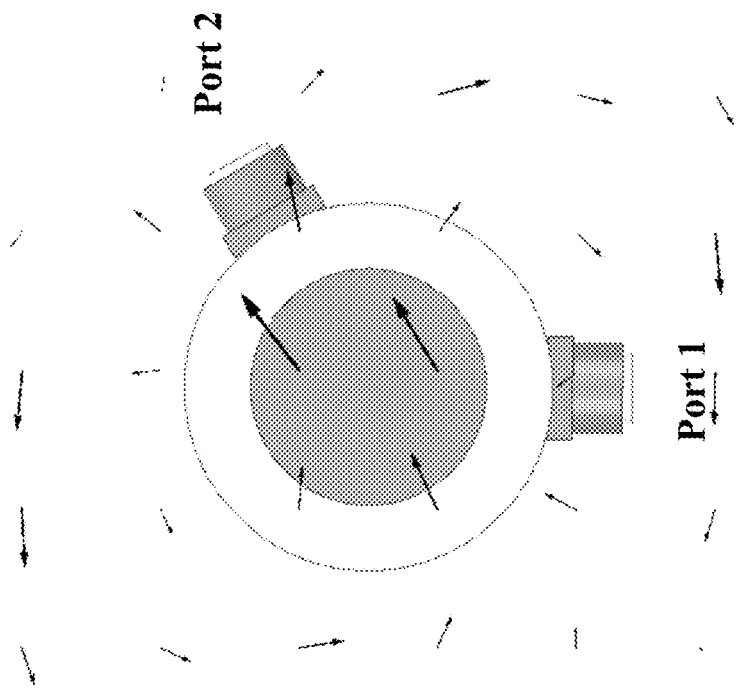
FIG. 52 shows a side-view of electric field polarization with two feeds at 120 degrees relative to each other, according to an embodiment.

FIG. 52 shows a side-view of electric field polarization with two feeds at 120 degrees relative to each other. Feed 1 is at 0 degrees phase and 0 percent power. Feed 2 is at 180 degrees phase and 100 percent power.

Figures 53, 54:
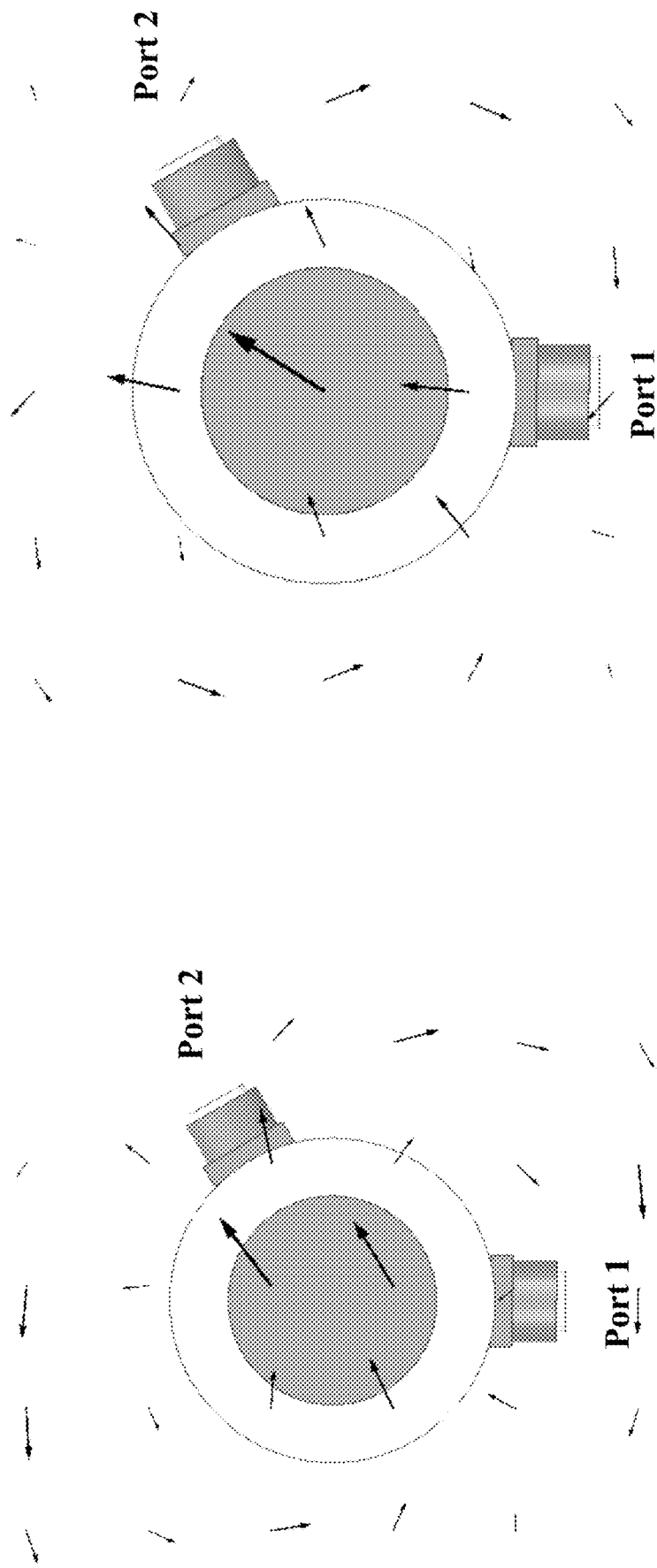
FIG. 53 shows a side-view of electric field polarization with two feeds at 120 degrees relative to each other, according to an embodiment.
FIG. 54 shows a side-view of electric field polarization with two feeds at 120 degrees relative to each other, according to an embodiment.

FIG. 53 shows a side-view of electric field polarization with two feeds at 120 degrees relative to each other. Feed 1 is at 180 degrees phase and 0 percent power. Feed 2 is at 180 degrees phase and 100 percent power.

FIG. 54 shows a side-view of electric field polarization with two feeds at 120 degrees relative to each other. Feed 1 is at 180 degrees phase and 50 percent power. Feed 2 is at 180 degrees phase and 50 percent power.

FIG. 55 shows a side-view of electric field polarization with two feeds at 120 degrees relative to each other. Feed 1 is at 180 degrees phase and 100 percent power. Feed 2 is at 180 degrees phase and 0 percent power.

FIG. 56 shows a side-view of electric field polarization with two feeds at 120 degrees relative to each other. Feed 1 is at 180 degrees phase and 100 percent power. Feed 2 is at 0 degrees phase and 0 percent power.

Figure 57:
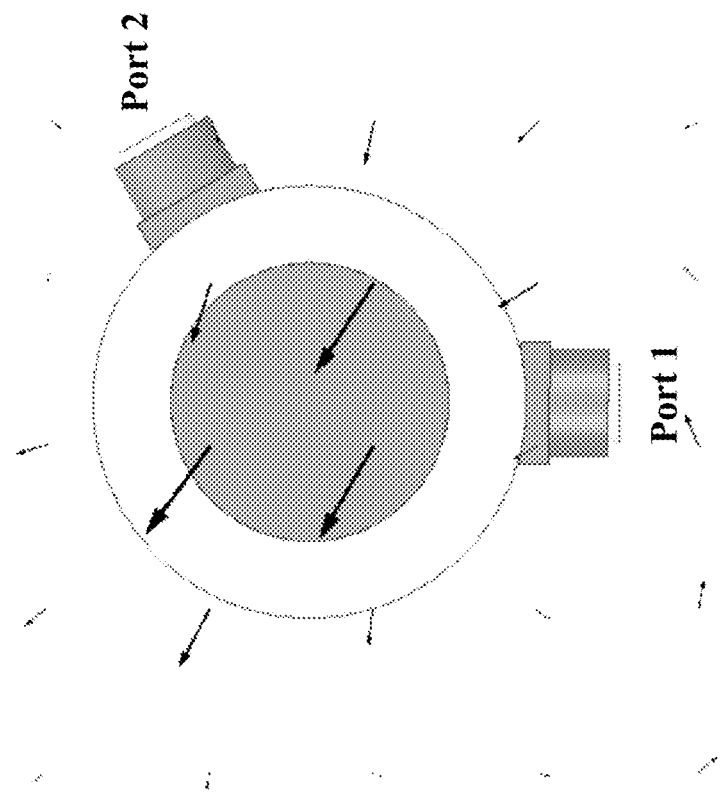
FIG. 57 shows a side-view of electric field polarization with two feeds at 120 degrees relative to each other, according to an embodiment.

FIG. 57 shows a side-view of electric field polarization with two feeds at 120 degrees relative to each other. Feed 1 is at 180 degrees phase and 50 percent power. Feed 2 is at 0 degrees phase and 50 percent power.

Figure 58:
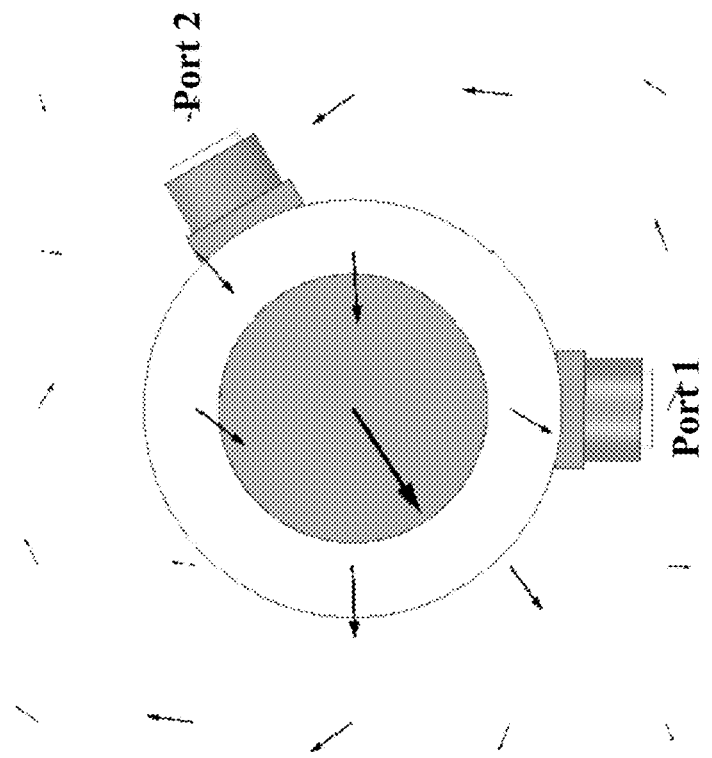
FIG. 58 shows a side-view of electric field polarization with two feeds at 120 degrees relative to each other, according to an embodiment.

FIG. 58 shows a side-view of electric field polarization with two feeds at 120 degrees relative to each other. Feed 1 is at 180 degrees phase and 0 percent power. Feed 2 is at 0 degrees phase and 100 percent power.

FIGS. 59A-59F show a side-view of electric field polarization with two feeds at 120 degrees relative to each other at six different points in a cycle, according to an embodiment. The electric field polarizations are shown at different phases of a cycle: 0 degrees, 72 degrees, 144 degrees, 216 degrees, 288 degrees, and 360 degrees (which is the same as 0 degrees).

FIG. 60 shows an isometric view of electric field polarization with two feeds at 120 degrees relative to each other at a varying distance into tissue. Feed 1 is at 0 degrees phase and 50 percent power. Feed 2 is at 90 degrees phase and 50 percent power. Directional energy vectors are shown rotating about an axis that is perpendicular to the center of the face of the RF applicator 312. These energy vectors rotate 360 degrees per cycle about the axis that is perpendicular to the center of the face of the RF applicator 312.

FIG. 61 shows a side-view of electric field polarization with two feeds at 120 degrees relative to each other at a varying distance into tissue. Feed 1 is at 0 degrees phase and 50 percent power. Feed 2 is at 90 degrees phase and 50 percent power. Directional energy vectors are shown rotating about an axis that is perpendicular to the center of the face of the RF applicator 312. These energy vectors rotate 360 degrees per cycle about the axis that is perpendicular to the center of the face of the RF applicator 312.

Although embodiments have been described above with reference to the accompanying drawings, those of skill in the art will appreciate that variations and modifications may be made without departing from the scope thereof as defined by the appended claims.

What is claimed is:

1. A thermoacoustic measurement probe comprising:
an open-ended hollow radio-frequency (RF) waveguide;
at least two RF feeds positioned within the open-ended hollow RF waveguide, wherein each RF feed is configured to provide RF energy; and
a thermoacoustic transducer,
wherein the open-ended hollow RF waveguide, in the form of a sleeve, surrounds and is mechanically joined to the thermoacoustic transducer.

2. The thermoacoustic measurement probe of claim 1, wherein each said RF feed comprises an axis and said RF feeds have parallel axes.

3. The thermoacoustic measurement probe of claim 1, wherein each said RF feed comprises an axis and said RF feeds have non-parallel axes.

4. The thermoacoustic measurement probe of claim 1, wherein the open-ended hollow RF waveguide comprises an open-ended hollow waveguide fill and an interior region, further wherein said at least two RF feeds are positioned within the open-ended hollow waveguide fill.

5. The thermoacoustic measurement probe of claim 1, wherein the at least two RF feeds comprise a first RF feed having a first phase and a second RF feed having a second phase different from the first phase.

6. The thermoacoustic measurement probe of claim 1, wherein the at least two RF feeds comprise a first RF feed at a first power level and a second RF feed at a second power level different from the first power level.

7. The thermoacoustic measurement probe of claim 1, wherein the at least two RF feeds comprise a first RF feed and a second RF feed at the same power level.

8. A thermoacoustic measurement probe comprising:
a radio-frequency (RF) waveguide having a cavity;
individual RF feeds positioned within the RF waveguide, wherein each individual RF feed is configured to provide RF energy at a different phase; and
a thermoacoustic transducer positioned in the cavity of the RF waveguide.

9. The thermoacoustic measurement probe of claim 8, wherein each said RF feed comprises an axis and said RF feeds have parallel axes.

10. The thermoacoustic measurement probe of claim 8, wherein each said RF feed comprises an axis and said RF feeds have non-parallel axes.

11. The thermoacoustic measurement probe of claim 8, wherein the open-ended hollow RF waveguide comprises an open-ended hollow waveguide fill and an interior region, further wherein said at least two RF feeds are positioned within the open-ended hollow waveguide fill.

12. The thermoacoustic measurement probe of claim 8, wherein the two individual RF feeds comprise a first RF feed having a first phase and a second RF feed having a second phase completely out of phase from the first phase.

13. The thermoacoustic measurement probe of claim 8, wherein the two individual RF feeds comprise a first RF feed at a first power level and a second RF feed at a second power level different from the first power level.

14. The thermoacoustic measurement probe of claim 8, wherein the two individual RF feeds comprise a first RF feed and a second RF feed at the same power level.

15. A thermoacoustic measurement probe comprising:
a cylindrical radio-frequency (RF) waveguide housing;

a plurality of RF feeds positioned within the RF waveguide housing, wherein each RF feed is configured to provide RF energy;
a cylindrical ceramic inside the cylindrical RF waveguide housing;
a cylindrical acoustic isolation inside of the cylindrical ceramic; and
a thermoacoustic sensor at an end of the cylindrical acoustic isolation.

16. The thermoacoustic measurement probe of claim 15, wherein each said RF feed comprises an axis and said RF feeds have parallel axes.

17. The thermoacoustic measurement probe of claim 15, wherein the plurality of RF feeds are located at 90 degrees relative to each other within the cylindrical RF waveguide housing.

18. The thermoacoustic measurement probe of claim 15, wherein each said RF feed comprises an axis and said RF feeds have non-parallel axes.

19. The thermoacoustic measurement probe of claim 15, wherein the open-ended hollow RF waveguide comprises an open-ended hollow waveguide fill and an interior region, further wherein said at least two RF feeds are positioned within the open-ended hollow waveguide fill.

20. The thermoacoustic measurement probe of claim 15, wherein the plurality of RF feeds comprise a first RF feed and a second RF feed at the same power level.

* * * * *